(12) United States Patent
Andersen et al.

(10) Patent No.: US 6,492,374 B2
(45) Date of Patent: Dec. 10, 2002

(54) BENZOFURAN DERIVATIVES, THEIR PREPARATION AND USE

(75) Inventors: Kim Andersen, Virum (DK); Mario Rottländer, Valby (DK); Klaus Peter Bøgesø, Hørsholm (DK); Henrik Pedersen, Brønshøj (DK); Thomas Ruhland, Valby (DK); Robert Dancer, Frederiksberg C (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/874,392

(22) Filed: Jun. 4, 2001

(65) Prior Publication Data
US 2002/0032205 A1 Mar. 14, 2002

Related U.S. Application Data

(63) Continuation of application No. PCT/DK99/00676, filed on Dec. 3, 1999.
(60) Provisional application No. 60/111,360, filed on Dec. 8, 1998.

(30) Foreign Application Priority Data

Dec. 9, 1998 (DK) .......................... 1998 01631

(51) Int. Cl.[7] ................... C07D 405/06; C07D 403/14; A61K 31/4439; A61K 31/44; A61P 25/24
(52) U.S. Cl. .................. 514/254.09; 548/466; 548/467; 544/376; 546/196; 546/201; 546/277.1; 546/284.4; 546/283.4; 514/469; 514/470; 514/337; 514/339; 514/326
(58) Field of Search ................................ 548/466, 467; 544/376; 514/469, 470, 339, 337, 254.09, 326; 546/201, 196, 277.1, 284.4, 283.4

(56) References Cited

U.S. PATENT DOCUMENTS 3,523,124 A 8/1970 Petersen et al. ......... 260/346.2
4,136,193 A 1/1979 Bøgesø et al. .............. 424/285

FOREIGN PATENT DOCUMENTS

WO    WO 95/18118    7/1995

*Primary Examiner*—Mark L. Berch
*Assistant Examiner*—Kahsay Habte
(74) *Attorney, Agent, or Firm*—Darby & Darby

(57) ABSTRACT

The present invention relates to benzofuran derivatives having general Formula (I)

(I)

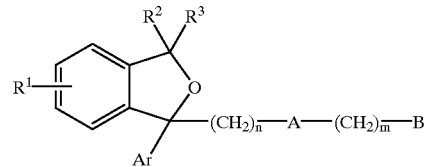

wherein A is selected from (1), (2), (3), (4)

(1)

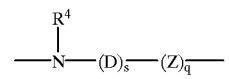

(2)

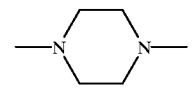

(3)

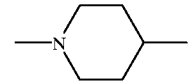

(4)

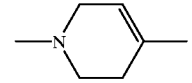

wherein

Z is O or S; s is 0 or 1; q is 0 or 1; $R^4$ is hydrogen, $C_{1-6}$-alkyl, $C_{2-6}$-alkenyl, $C_{2-6}$-alkynyl, $C_{1-6}$-alkyl-aryl, or $C_{1-6}$-alkyl-O-aryl; D is a spacer group selected from branched or straight chain $C_{1-6}$-alkylene, $C_{2-6}$-alkenylene and $C_{2-6}$-alkynylene; its enantiomers, and pharmaceutically acceptable acid addition salt thereof. The compounds are potently binding to the $5\text{-HT}_{1A}$ receptor.

34 Claims, No Drawings

BENZOFURAN DERIVATIVES, THEIR PREPARATION AND USE

This is a continuation of international application Serial No. PCT/DK99/00676, filed Dec. 3, 1999, the entire disclosure of which is hereby incorporated by reference, which claims priority under 35 U.S.C. §119 of U.S. provisional application Ser.No. 60/111,360, filed Dec. 8, 1998.

The present invention relates to novel benzofuran derivatives potently binding to the 5-$HT_{1A}$ receptor, pharmaceutical compositions containing these compounds and the use thereof for the treatment of certain psychiatric and neurological disorders. Many of the compounds of the invention are also potent serotonin reuptake inhibitors and are considered to be particularly useful for the treatment of depression.

BACKGROUND ART

Clinical studies of known 5-$HT_{1A}$ partial agonists such as e.g. buspirone, ipsapirone and gepirone have shown that 5-$HT_{1A}$ partial agonists are useful in the treatment of anxiety disorders such as generalised anxiety disorder, panic disorder, and obsessive compulsive disorder (Glitz, D. A., Pohl, R., *Drugs* 1991, 41, 11). Preclinical studies indicate that full agonists also are useful in the treatment of the above mentioned anxiety related disorders (Schipper, *Human Psychopharm.*, 1991, 6, S53).

There is also evidence, both clinical and preclinical, in support of a beneficial effect of 5-$HT_{1A}$ partial agonists in the treatment of depression as well as impulse control disorders and alcohol abuse (van Hest, *Psychopharm.*, 1992, 107, 474; Schipper et al, *Human Psychopharm.*, 1991, 6, S53; Cervo et al, *Eur. J. Pharm.*, 1988, 158, 53; Glitz, D. A., Pohl, R., *Drugs* 1991, 41, 11; Grof et al., *Int. Clin. Psychopharmacol.* 1993, 8, 167–172; Ansseau et al., *Human Psychopharmacol.* 1993, 8, 279–283).

5-$HT_{1A}$ agonists and partial agonists inhibit isolation-induced aggression in male mice indicating that these compounds are useful in the treatment of aggression (Sanchéz et al, *Psychopharmacology*, 1993, 110, 53–59).

Furthermore, 5-$HT_{1A}$ agonists have been reported to show activity in animal models predictive for antipsychotic effects (Wadenberg and Ahlenius, *J. Neural. Transm.*, 1991, 83,43; Ahlenius, *Pharmacol. & Toxicol.*, 1989, 64, 3; Lowe et al., *J. Med. Chem.*, 1991, 34, 1860; New et al., *J. Med. Chem.*, 1989, 32, 1147; and Martin et al., *J. Med Chem.*, 1989, 32, 1052) and may therefore be useful in the treatment of psychotic disorders such as schizophrenia. Recent studies also indicate that 5-$HT_{1A}$ receptors are important in the serotonergic modulation of haloperidol-induced catalepsy (Hicks, *Life Science* 1990, 47, 1609) suggesting that 5-$HT_{1A}$ agonists are useful in the treatment of the side effects induced by conventional antipsychotic agents such as e.g. haloperidol.

5-$HT_{1A}$ agonists have shown neuroprotective properties in rodent models of focal and global cerebral ischaemia and may, therefore, be useful in the treatment of ischaemic disease states (Prehn , *Eur. J. Pharm.* 1991, 203, 213).

Pharmacological studies have been presented which indicate that 5-$HT_{1A}$ antagonists are useful in the treatment of senile dementia (Bowen et al., Trends Neur. Sci. 1992, 15, 84).

An overview of 5-$HT_{1A}$ antagonists and proposed potential therapeutic targets for these antagonists based upon preclinical and clinical data are presented by Schechter et al., *Serotonin*, 1997, Vol.2, Issue 7. It is stated that 5-$HT_{1A}$ antagonists may be useful in the treatment of schizophrenia, dementia associated with Alzheimer's disease, and in combination with SSRI antidepressants also to be useful in the treatment of depression.

Both in animal models and in clinical trials it has been shown that 5-$HT_{1A}$ agonists exert antihypertensive effects via a central mechanism (Saxena and Villalón, *Trends Pharm. Sci.* 1990, 11, 95; Gillis et al, *J. Pharm. Exp. Ther.* 1989, 248, 851). 5-$HT_{1A}$ ligands may, therefore, be beneficial in the treatment of cardiovascular disorders.

5-HT reuptake inhibitors are well known antidepressant drugs and useful for the treatment of panic disorders and social phobia The effect of combined administration of a compound that inhibits serotonin reuptake and a 5$HT_{1A}$ receptor antagonist has been evaluated in several studies (Innis, R. B. et al., *Eur. J. Pharmacol.*, 1987, 143, p 195–204 and Gartside, S. E., *Br. J. Pharmacol.* 1995, 115, p 1064–1070, Blier, P. et al, *Trends Pharmacol. Sci.* 1994, 15, 220). In these studies it was found that 5-$HT_{1A}$ receptor antagonists would abolish the initial brake on 5-HT neurotransmission induced by the serotonin reuptake inhibitors and thus produce an immediate boost of 5-HT transmission and a more rapid onset of therapeutic action.

Several patent applications have been filed which cover the use of a combination of a 5-$HT_{1A}$ antagonist and a serotonin reuptake inhibitor for the treatment of depression (see EP-A2-687 472 and EP-A-714 663).

Accordingly, agents acting on the 5-$HT_{1A}$ receptor, both agonists and antagonists, are believed to be of potential use in the therapy of psychiatric and neurological disorders and thus being highly desired. Furthermore, antagonists at the same time having potent serotonin reuptake inhibition activity may be useful for the treatment of depression.

SUMMARY OF THE INVENTION

It has now been found that compounds of a certain class of benzofuran derivatives bind to the 5-$HT_{1A}$ receptor with high affinities. Furthermore, it has been found that many of these compounds have potent serotonin reuptake inhibition activity.

Accordingly, the present invention relates to novel compounds of the general Formula I:

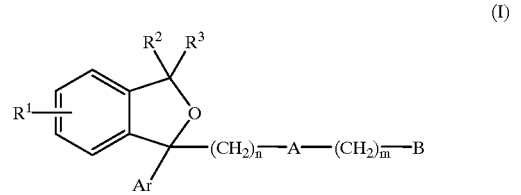

(I)

wherein

R$^1$ is hydrogen, halogen, trifluoromethyl, trifluoromethylsulfonyloxy, $C_{1-6}$ alkyl, $C_{2-6}$ alkenyl, $C_{2-6}$ alkynyl, $C_{3-8}$ cycloalkyl, $C_{1-6}$ alkoxy, hydroxy, formyl, acyl, amino, $C_{1-6}$ alkylamino, $C_{2-12}$ dialkylamino, acylamino, $C_{1-6}$ alkoxycarbonylamino, aminocarbonylamino, $C_{1-6}$ alkylaminocarbonylamino, $C_{2-12}$ dialkylaminocarbonylamino, nitro, cyano, COOH, or COO—$C_{1-6}$ alkyl;

R$^2$ and R$^3$ are each independently selected from hydrogen, tifluoromethyl, $C_{1-6}$ alkyl, $C_{2-6}$ alkenyl, $C_{2-6}$ alkynyl, $C_{3-8}$ cycloalkyl and $C_{1-6}$ alkoxy;

n is 1, 2, 3, 4 or 5;

m is 0 or 1;

A is selected from the following groups:

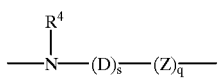
(1)

(2)

(3)

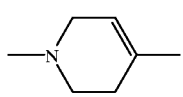
(4)

wherein

Z is O or S;

s is 0 or 1;

q is 0 or 1;

$R^4$ is hydrogen, $C_{1-6}$-alkyl, $C_{2-6}$-alkenyl, $C_{2-6}$alkynyl, $C_{1-6}$alkyl-Aryl, or $C_{1-6}$-alkyl-O-Aryl, D is a spacer group selected from branched or straight chain $C_{1-6}$-alkylene, $C_{2-6}$-alkenylene and $C_{2-6}$-alkynylene;

B is a group selected from a group of formula (II), (III), and (IV)

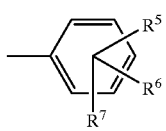
(II)

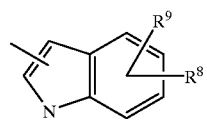
(III)

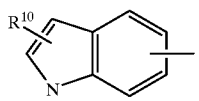
(IV)

wherein $R^5$, $R^6$, $R^7$, $R^8$, $R^9$ and $R^{10}$ are each independently selected among the $R^1$ substituents;

or $R^8$ and $R^9$ together form a fused 5- or 6-membered ring optionally containing further heteroatoms;

or two of the groups of $R^5$, $R^6$ and $R^7$ are linked together thereby forming a —O—$(CH_2)_p$—O—-bridge wherein p is 1 or 2;

Ar and Aryl are independently selected from the group consisting of phenyl, 2-thienyl, 3-thienyl, 2-furanyl, 3-furanyl, 2-pyrimidyl, 1-indolyl, 2-indolyl, 3-indolyl, indol-2-on-1-yl, indol-2-on-3-yl, 2- or 3-benzofuranyl, 2- or 3-benzothiophenyl, 1-naphthyl or 2-naphthyl, each optionally substituted with halogen, $C_{1-6}$ alkyl, $C_{1-6}$ alkoxy, $C_{1-6}$ alkylthio, hydroxy, $C_{1-6}$ alkylsulfonyl, cyano, trifluoromethyl, trifluoromethylsulfonyloxy, $C_{3-8}$ cycloalkyl, $C_{3-8}$cycloalkyl-$C_{1-6}$ alkyl, nitro, amino, $C_{1-6}$ alkylamino, $C_{2-12}$ dialkylamino, acylamino or alkylenedioxy;

its enantiomers, and pharmaceutically acceptable acid addition salt thereof.

In one embodiment of the invention A is a group of formula (1) and the other substituents are as defined above.

In another embodiment of the invention A is a group of formula (2) and the other substituents are as defined above.

In a third embodiment of the invention A is a group of formula (3) and the other substituents are as defined above.

In a fourth embodiment of the invention A is a group of formula (4) and the other substituents are as defined above.

Thus in a preferred embodiment of the invention A is a group of formula (1) and $R^4$ is methyl, ethyl, propyl, prop-2-en-1-yl, 2-furylmethyl, or 2-phenoxyethyl; q=0; or A is a group of formula (1) and Z is O and the other substituents are as defined above.

In a further embodiment of the invention, B is a group of formula (II), preferably a alkoxysubstituted phenyl, a benzodioxan group or a 1,2-methylenedioxybenzene group and the other substituents are as defined above.

In a further embodiment of the invention, B is a group of formula (III), preferably a 3-indolyl group and the other substituents are as defined above.

In a further embodiment of the invention, B is a group of formula (HI), preferably a 3-indolyl group and the substituents $R^8$ and $R^9$ are preferably selected from hydrogen, methyl, fluoro, chloro, bromo, iodo, t-butyl or i-propyl in the 5-position; or fluoro, chloro or carboxy in the 7-position; or by 5,7-difluoro, 4-fluoro-7-methyl or 4-chloro-7-methyl; or the two substituents together form a pyridyl ring fused to the 3-indolyl.

In a further embodiment of the invention, B is a group of formula (IV) and the other substituents are as defined above.

Ar is preferably phenyl or phenyl substituted with halogen or $CF_3$, most preferably substituted with F or Cl in the 4-position or Cl or $CF_3$ in the 3-position.

$R^1$ is preferably H, CN or F in the 5-position of the isobenzofuran group.

$R^2$ and $R^3$ are preferably selected from hydrogen or methyl.

n is preferably 2, 3 or 4.

m is preferably 0.

In a preferred embodiment of the invention n=2, 3 or 4; $R^2$ and $R^3$ are both hydrogen; $R^1$ is H, CN or F in the 5-position of the isobenzofuran group; and Ar is phenyl which may be substituted with F or Cl in the 4-position or with Cl or $CF_3$ in the 3-position and the other substituents are as defined above.

In another preferred embodiment of the invention, A is a group of formula (1); q=0; $R^4$ is methyl; D is propylene; m=0; and B is a 1,4-benzodioxan group of Formula (II) attached in the 5-position and the other substituents are as defined above.

In another preferred embodiment of the invention, A is a group of formula (1); $R^4$ is $CH_3$ or prop-2-en-1-yl; n=3; D is ethylene or propylene; and B is a phenyl group wherein at least one substituent is OMe and the other substituents are as defined above.

In a further embodiment of the invention, A is a group of formula (1); q is 0; $R^4$ is methyl, ethyl, propyl, 2-propen-1-yl, 2-furylmethyl or 2-phenoxyethyl; D is ethylene, propylene or butylene; m=0; and B is a 3-indolyl group of Formula (III) and the other substituents are as defined above.

In another preferred embodiment of the invention, A is a group of formula (2) or (3); n=3; m=0; and B is an 4- or 5-indolyl-group of Formula (IV) wherein $R^{10}$ is hydrogen; $R^1$ is CN in the 5-position of the isobenzofuran and Ar is 4-Fluorophenyl and the other substituents are as defined above.

The invention also relates to a pharmaceutical composition comprising a compound of formula (I) or a pharmaceutically acceptable salt thereof and at least one pharmaceutically acceptable carrier or diluent.

In a further embodiment, the invention relates to the use of a compound of formula (I) or a pharmaceutically acceptable acid addition salt thereof for the preparation of a medicament for the treatment of a disorder or disease responsive to the effect of $5\text{-HT}_{1A}$ receptors.

In particular, the invention relates to the use of a compound according to the invention or a pharmaceutically acceptable acid addition salt thereof for the preparation of a medicament for the treatment of depression, psychosis, anxiety disorders, panic disorder, obsessive compulsive disorder, impulse control disorder, alcohol abuse, aggression, ischaemia, senile dementia, cardiovascular disorders or social phobia.

In still another embodiment, the present invention relates to a method for the treatment of a disorder or disease of living animal body, including a human, which is responsive to the effect of $5\text{-HT}_{1A}$ receptors comprising administering to such a living animal body, including a human, a therapeutically effective amount of a compound of formula (I) or a pharmaceutically acceptable acid addition salt thereof.

The compounds of the invention have high affinity for the $5\text{-HT}_{1A}$ receptor. Accordingly, the compounds of the invention are considered useful for the treatment of depression, psychosis, anxiety disorders, such as generalised anxiety disorder, panic disorder, and obsessive compulsive disorder, impulse control disorder, alcohol abuse, aggression, ischaemia, senile dementia, cardiovascular disorders and social phobia.

Due to their combined antagonism of $5\text{-HT}_{1A}$ receptors and serotonin reuptake inhibiting effect, many of the compounds of the invention are considered particularly useful as fast onset of action medicaments for the treatment of depression. The compounds may also be useful for the treatment of depression in patients who are resistant to treatment with currently available antidepressants.

DETAILED DESCRIPTION OF THE INVENTION

Some of the compounds of general Formula I may exist as optical isomers thereof and such optical isomers are also embraced by the invention.

The term $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, inclusive.

Halogen means fluoro, chloro, bromo, or iodo.

The term $C_{3-8}$ cycloalkyl designates a monocyclic or bicyclic carbocycle having three to eight C-atoms, such as cyclopropyl, cyclopentyl, cyclohexyl, cycloheptyl, and cyclooctyl.

The terms $C_{1-6}$ alkoxy, $C_{1-6}$ alkylthio, $C_{1-6}$ alkylsulfonyl, designate such groups in which the alkyl group is $C_{1-6}$ alkyl as defined above.

Acyl means —CO-alkyl wherein the alkyl group is $C_{1-6}$ alkyl as defined above.

$C_{1-6}$ alkylamino means —NH-alkyl, and $C_{2-12}$ dialkylamino means —N-(alkyl)$_2$ where the alkyl group is $C_{1-6}$ alkyl as defined above.

Acylamino means —NH-acyl wherein acyl is as defined above.

$C_{1-6}$ alkoxycarbonylamino means alkyl-O—CO—NH— wherein the alkyl group is $C_{1-6}$ alkyl as defined above.

$C_{1-6}$ alkylaminocarbonylamino means alkyl-NH—CO—NH— wherein the alkyl group is $C_{1-6}$ alkyl as defined above.

$C_{2-12}$ dialkylaminocarbonylamino means (alkyl)$_2$—N—CO—NH— wherein the alkyl group is $C_{1-6}$ alkyl as defined above.

Exemplary of organic acid addition salts according to the invention are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of inorganic acid addition salts according to the invention are those with hydrochloric, hydrobromic, sulfuric, sulfamic, phosphoric, and nitric acids. The acid addition salts of the invention are preferably pharmaceutically acceptable salts formed with non-toxic acids.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (e.g. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallisation of d- or l- (tartrates, mandelates, or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet, and S. Wilen in "Enantiomers, Racemates, and Resolutions", John Wiley and Sons, New York (1981).

Optically active compounds can also be prepared from optically active starting materials.

The compounds of the invention can be prepared by one of the following methods comprising:

a) alkylating an amine of formula (V)

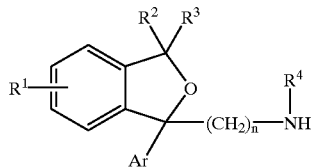

wherein $R^1$, $R^2$, $R^3$, $R^4$, n and Ar are as defined above with an alkylating agent of formula G—$(D)_s$—$(Z)_q$—$(CH_2)_m$—B wherein D, Z, m, s, q and B are as defined above and G is a suitable leaving group such as halogen, mesylate, or tosylate;

b) alkylating an amine of formula H—A—$(CH_2)_m$—B wherein A, m and B are as defined above with an alkylating agent of formula (VI)

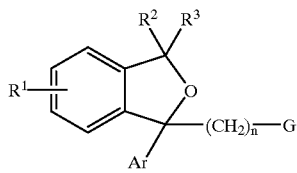

wherein $R^1$, $R^2$, $R^3$, n and Ar are as defined above and G is a suitable leaving group such as halogen, mesylate, or tosylate;

c) reductive alkylation of an amine of formula (VII)

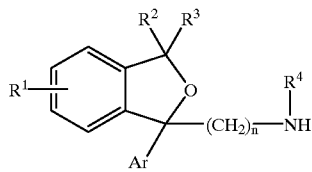

wherein $R^1$, $R^2$, $R^3$, $R^4$, n and Ar are as defined above with an aldehyde of formula (VIII)

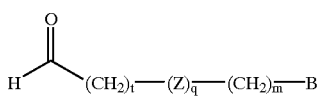

wherein Z, m, q and B are as defined above and t is 1–5;

d) reducing an amide of formula (XI)

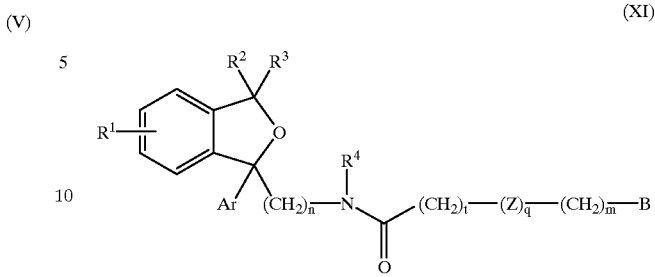

wherein $R^1$, $R^2$, $R^3$, $R^4$, n, q, Ar, Z, m and B are as defined above and t is 1–5;

e) releasing final product by the means of Hofmann elimination from a resin of formula (XII)

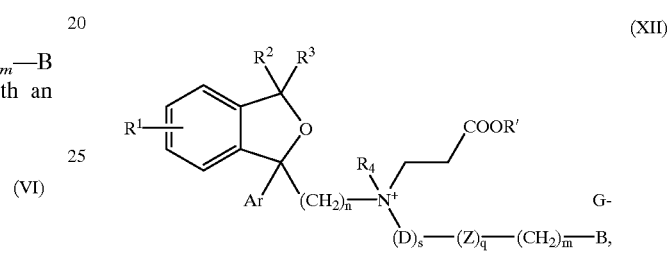

wherein $R^1$, $R^2$, $R^3$, $R^4$, n, s, q, Ar, D, Z, m and B are as defined above, G is defined above; and HOR' is a hydroxy substituted resin such as cross linked hydroxymethylpolystyrene or Wang resin.

f) reacting a compound of the formula

XIII

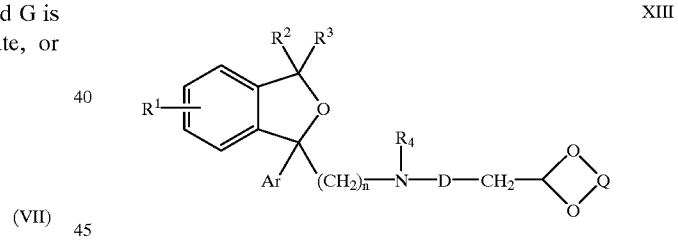

wherein $R^1$, $R^2$, $R^3$, $R^4$, Ar, D and N are as defined above; $(OH)_2Q$ is a diol such as substituted ethylene glycol or propylene glycol, or a polymer bound diol, with a hydrazine of formula

XIV

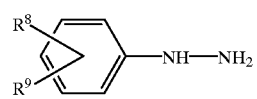

wherein $R^8$ and $R^9$ is as defined above, using Lewis acids as catalyst.

The alkylations according to Methods a and b are generally performed by boiling the reactants under reflux or by heating them at a fixed temperature in a suitable solvent such as acetone, methyl isobutyl ketone, tetrahydrofuran, dioxane, ethanol, 2-propanol, ethyl acetate, N,N-dimethylformamide, dimethyl sulfoxide or 1-methyl-2-pyrrolidinone in the presence of a base such as triethylamine or potassium carbonate. Amines of formula V are prepared by means of demethylation according to the method described by Bigler et al, Eur. J. Med. Chem. Chim. Ther, 1977, 12, 289–295, or by the methods outlined in examples 14 and 15. The starting materials used in example 14 were prepared as described in example 9 or from readily available compounds by standard methods. The enantiomers of 1-[3-(dimethylamino)propyl]-1-(4-fluorophenyl)-1,3-dihydroisobenzofuran-5-carbonitrile used as starting material for the demethylation are prepared as described in EP patent No. 347066. The alkylating agents of formula G—(D)$_s$ —(Z$_q$—(CH$_2$)$_m$—B are commercially available, prepared by methods obvious to the chemist skilled in the art or prepared as exemplified in Examples 5–8. Ethyl 1,4-benzodioxan-5-carboxylate used as starting material in Example 5 is prepared by methods obvious to the chemist skilled in the art from the corresponding carboxylic acid prepared according to literature (Fuson et al., J. Org. Chem., 1948, 13, 489). Alkylating agents of formula VI are prepared from the corresponding dimethylamine (Formula VI: G=N(Me)$_2$) as exemplified in example 9. The secondary amines of formula H—A—(CH$_2$)$_m$—B are commercially available, prepared by methods obvious to the chemist skilled in the art or prepared according to literature procedures. 1-(2-methoxyphenyl)piperazine is prepared according to Pollard et al., J. Org. Chem., 1958, 23, 1333. [2-(2-Methoxyphenoxy)ethyl]methylamine and [2-(3-methoxyphenoxy)ethyl]-methylamine are prepared as exemplified in Examples 7 and 10 using commercially available 2-methoxyphenoxyacetic acid and 3-methoxyphenoxyacetic acid, respectively, as starting materials.

The reductive alkylations according to method c and d are performed according to standard literature methods using NaCNBH$_3$, NaBH$_4$ or NaBH(OAc)$_3$ as reducing agent in a suitable solvent.

The reductions according to Methods e and f are generally performed by use of LiAlH$_4$, AlH$_3$ or diborane in an inert solvent such as tetrahydrofuran, dioxane, or diethyl ether at room temperature or at a slightly elevated temperature.

The release of final products by means of Hofmann elimination in Method g is generally performed by the use of an organic base such as triethylamine or diisopropylethylamine in an aprotic organic solvent such as dichloromethane, toluene or N,N-dimethylformamide. The polymer of formula XII is prepared in a synthesis sequence as exemplified in Example 4 and described in the following. The starting acryl ester resin (CH$_2$CHC(O)OR') is prepared according to literature procedures (Brown et al., J. Am. Chem. Soc., 1997, 119, 3288–95) by acylation of commercially available hydroxy substituted resins such as cross linked hydroxymethylpolystyrene or Wang resin with acryloyl chloride. Secondary amines of formula H$_2$N—D—Z—(CH$_2$)$_m$—B are introduced by Michael addition in an organic solvent such as N,N-dimethylformamide at ambient temperature. The secondary amines used are either commercially available, prepared by methods obvious to the chemist skilled in the art or prepared according to literature procedures. 3-(2-Methoxyphenyl)propylamine is prepared according to Leeson et al., J. Med. Chem. 1988, 31, 37–54, 3-(3-methoxyphenyl)propylamine according to Meise et al. Liebigs Ann. Chem., 1987, 639–42, 3-(2-methoxyphenoxy)propylamine according to Augsein et al., J. Med. Chem., 1965, 8, 356–67, 3-(3-methoxyphenoxy)propylamine according to Brenner et al., Aust. J. Chem. 1984, 37, 129–41, 2-benzyloxyethylamine according to Harder et al. Chem. Ber. 1964, 97, 510–19, 2-(1H-indolyl-3-yl)ethylamine according to Nenitzescu et al., Chem. Ber., 1958, 91, 1141–45 and 3-(1H-indolyl-3-yl)propylamine according to Jackson et al., J. Am. Chem. Soc., 1930, 52, 5029. The second diversifying group is introduced by means of alkylation with an agent of formula VI by boiling the reactants under reflux or by heating them at a fixed temperature in a suitable solvent such as tetrahydrofuran, dioxane, ethanol, 2-propanol, ethyl acetate, N,N-dimethylformamide, dimethyl sulfoxide or 1-methyl-2-pyrrolidinone in the presence of a soluble base such as diisopropylethylamine or triethylamine, or by means of reductive alkylation with an aldehyde of formula IX using standard solid phase synthesis literature methods using NaCNBH$_3$, NaBH$_4$ or NaBH(OAc)$_3$ as reducing agent in a suitable solvent. The third diversifying group was introduced by means of quarternisation using an alkylating agent of formula R$^4$-G in an organic solvent such as tetrahydrofuran, dioxane, ethanol, 2-propanol, ethyl acetate, N,N-dimethylformamide, dimethyl sulfoxide or 1-methyl-2-pyrrolidinone at ambient temperature giving resins of formula XII.

The indole formation according to method h is performed by the reaction of acetals of formula XIII with aryl hydrazines of formula XIV resulting in the corresponding hydrazones, which subsequently are converted into indoles by means of the Fischer indole synthesis. The synthesis sequence is preferably performed as a one-pot procedure using a Lewis acid catalysts, preferably zinc chloride or boron fluoride, or protic acids, preferably sulfuric acid or phosphoric acid, in a suitable solvent such as acetic acid or ethanol at an elevated temperature. Acetals of formula XIII are prepared by alkylation of secondary amines of formula V with acetals of formula XV

XV

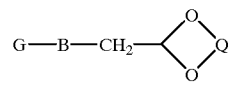

using the conditions described above for methods a and b. Alternatively, the acetals of formula XIII are prepared by alkylation of acetals of formula XVI

XVI

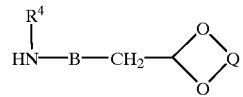

with an alkylating agent of formula VI using the conditions described above for methods a and b. The acetals of formula XVI are prepared by reaction of acetals of formula XV with primary amines of formula NH$_2$R$^4$ using standard conditions.

Polymer bound acetals of formula XV is prepared by reaction of aldehydes of formula G—B—CH$_2$CHO with commercially available 2,2-dimethyl-1,3dioxolan4-yl-methoxymethyl polystyrene in a suitable solvent such as toluene, using p-toluenesulfonic acid as catalyst at elevated temperature. 4-Chlorobutanal, 5-chloropentanal, and 6-chlorohexanal were prepared in analogy to the method described by Normant et al., Tetrahedron 1994, 50 (40), 11665.

EXAMPLES

Melting points were determined on a Buchi SMP-20 apparatus and are uncorrected. Mass spectra were obtained on a Quattro MS-MS system from VG Biotech, Fisons Instruments. The MS-MS system was connected to an HP 1050 modular HPLC system. A volume of 20–50 μl of the sample (10 μg/ml) dissolved in a mixture of 1% acetic acid in acetonitril/water 1:1 was introduced via the autosampler at a flow of 30 μl/min into the Electrospray Source. Spectra were obtained at two standard sets of operating conditions. Analytical LC-MS data were obtained on a PE Sciex API 150EX instrument equipped with Ionspray source and Shimadzu LC-8A/SLC-IOA LC system. The LC conditions (50×4.6 mm YMC ODS-A with 5 μm particle size) were linear gradient elution with water/acetonitrile/trifluoroacetic acid (90:10:0.05) to water/acetonitrile/trifluoroacetic acid (10:90:0.03) in 7 min at 2 mL/min. Purity was determined by integration of the UV trace (254 nm). The retention times $R_t$ are expressed in minutes.

One set to obtain molecular weight information (MH+) (21 eV) and the other set to induce fragmentation patterns (70 eV). The background was subtracted. The relative intensities of the ions are obtained from the fragmentation pattern. When no intensity is indicated for the Molecular Ion (MH+), this ion was only present under the first set of operating conditions. Preparative LC-MS-separation was performed on the same instrument. The LC conditions (50×20 mm YMC ODS-A with 5 μm particle size) were linear gradient elution with water/acetonitrile/trifluoroacetic acid (80:20:0.05) to water/acetonitrile/trifluoroacetic acid (10:90:0.03) in 7 min at 22.7 mL/min. Fraction collection was performed by split-flow MS detection.

$^1$H NMR spectra were recorded at 500.13 MHz on a Bruker Avance DRX500 instrument or is at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography silica gel of type Kieselgel 60, 230–400 mesh ASTM was used.

Example 1

(+)-1-[3-[[4-(1,4-Benzodioxan-5-yl)butyl]methylamino]propyl]-1-(fluorophenyl)-1,3-dihydroisobenzofuran-5-carbonitrile (1a). A mixture of 5-(4bromobutyl)-1,4-benzodioxane (1.5 g, 5.5 mmol), (+)-1-[3-(methylamino)propyl]-1-(4-fluorophenyl)-1,3-dihydroisobenzofuran-5-carbonitrile (2.2 g, 5.5 mmol), potassium carbonate (3.0 g, 22 mmol), and methyl isobutyl ketone (150 mL) was boiled under reflux for 16 h. After cooling to room temperature the organic phase was washed with water (150 mL), the solvents evaporated in vacuo and the remaining oil purified by column chromatography (ethyl acetate/heptane/triethylamine 75:20:5) affording 2.0 g (73%) of the title compound as an oil: $[\alpha]^{22}_D$+8.93° (c 0.5; $CH_3OH$). $^1$H NMR ($CDCl_3$) δ 1.25–1.35 (m, 1H), 1.40–1.60 (m, 5H), 2.05–2.30 (m, 9H), 2.55 (t, 2H), 4.20–4.30 (m, 4H), 5.10–5.20 (m, 2H), 6.65–6.75 (m, 3H), 7.00 (t, 2H), 7.35 (d,1H), 7.40 (dd, 2H), 7.50 (s, 1H), 7.60 (d, 1H); MS m/z 501 (MH+, 100), 262 (27), 149 (77), 109 (52).

The following compounds were prepared analogously:

(+)-1-[3-[[3-(1,4-Benzodioxan-5-yl)propyl]methylamino]propyl]-1-(4-fluorophenyl)-1,3-dihydroisobenzofuran-5-carbonitrile oxalate (1b): mp 114–16° C. (ethyl acetate);$[\alpha]^{22}_D$+8.96° (c 1.0; $CH_3OH$); $^1$H NMR (DMSO-$d_6$) δ 1.35–1.45 (m, 1H), 1.45–1.55 (m, 1H), 1.80 (m, 2H), 2.20–2.30 (m, 2H), 2.45–2.55 (m, 2H), 2.60 (s, 3H), 2.90 (m, 2H), 2.95 (m, 2H), 4.20–4.30 (m, 4H), 5.20 (m, 2H), 6.65–6.75 (m, 3H), 7.10–7.20 (m, 2H), 7.55–7.60 (m, 2H), 7.70–7.80 (m, 1H), 7.80–7.95 (m, 2H); MS m/z 488 (MH+, 100), 262 (33), 149 (52), 109 (55).

1-[3-[[2-(1,4-Benzodioxan-5-yl)ethyl]methylamino]propyl]-1-(4-fluorophenyl)-1,3-dihydroisobenzofuran-5carbonitrile oxalate (1c): mp 118–20° C. (ethyl acetate); $^1$H NMR (DMSO-$d_6$) δ 1.40–1.70 (m, 2H), 2.25 (t, 2H), 2.70 (s, 3H), 2.75–2.90 (m, 2H), 2.90–3.15 (m, 4H), 4.15–4.30 (m, 4H), 5.20 (m, 2H), 6.65–6.80 (m, 3H), 7.20 (t, 2H), 7.60 (dd, 2H), 7.70–7.85 (m, 3H); MS m/z 473 (ME+, 64), 323 (13), 262 (24), 163 (100), 109 (25).

1-[3-[[1,4-Benzodioxan-5-ylmethyl]methylamino]propyl]-1-(4fluorophenyl)-1,3-dihydroisobenzofuran-5-carbonitrile oxalate (1d): mp 160–62° C. (acetone/methanol); $^1$H NMR (DMSO-$d_6$) δ 1.40–1.70 (m, 2H), 2.25 (t, 2H), 2.60 (s, 3H), 2.90 (t, 2H), 4.00 (s, 2H), 4.20–4.30 (m, 4H), 5.20 (m, 2H), 6.80–7.00 (m, 3H), 7.15 (t, 2H), 7.50–7.65 (dd, 2H), 7.70–7.85 (m, 3H); MS m/z 459 (MH+, 7), 109 (100).

Example 2

1-(4-Fluorophenyl)-1-[3-[4-(2-methoxyphenyl)piperazinyl]propyl]-1,3-dihydroisobenzofuran-5-carbonitrile (2a). A mixture of 1-(3-chloropropyl)-1-(4-fluorophenyl)-1,3-dihydroisobenzofuran-5-carbonitrile (2.5 g, 7.9 mmol), 1-(2-methoxyphenyl)piperazine (2.0 g, 10.4 mmol), potassium carbonate (3 g, 22 mmol) and methyl isobutyl ketone (200 mL) was boiled under reflux for 16 h. After cooling to room temperature the organic phase was washed with water (200 mL), the solvents were evaporated in vacuo and the remaining oil purified by column chromatography (ethyl acetate/heptane/triethylamine 75:20:5). The title compound crystallised from diethyl ether 1.5 g (40 %): mp 147–49° C.; $^1$H NMR (DMSO-$d_6$) δ 1.30–1.65 (m, 2H), 2.10–2.30 (m, 2H), 2.40 (t, 2H), 2.50–2.70 (m, 4H), 2.90–3.20 (m, 4H), 3.85 (s, 3H), 5.20 (m, 2H), 6.70–7.10 (m, 6H), 7.30–7.55 (m, 4H), 7.60 (d, 1H); MS m/z, 472 (MH+, 100), 262 (14), 109 (19).

The following compounds were prepared analogously:

1-(4-Fluorophenyl)-1-[3-[[2-(2-methoxyphenoxy)ethyl]methylamino]propyl]-1,3-dihydroisobenzofuran-5-carbonitrile (2b): (oil) $^1$H NMR ($CDCl_3$) δ 1.30–1.40 (m, 1H), 1.40–1.55 (m, 1H), 2.10–2.20 (m, 2H), 2.25 (s, 3H), 2.40–2.45 (t, 2H), 2.70–2.80 (m, 2H), 3.70 (s, 3H), 4.05 (t, 2H), 5.15 (m, 2H), 6.85–7.00 (m, 6H), 7.30–7.45 (m, 3H), 7.50 (s, 1H), 7.55 (d, 1H).

1-(4-Fluorophenyl)-1-[3-[[2-(3-methoxyphenoxy)ethyl]methylamino]propyl]-1,3-dihydroisobenzofuran-5carbonitrile (2c): (oil) $^1$H NMR ($CDCl_3$) δ 1.30–1.40 (m, 1H), 1.40–1.55 (m, 1H), 2.10–2.20 (m, 2H), 2.25 (s, 3H), 2.40 (t, 2H), 2.70–2.75 (m, 2H), 3.70 (s, 3H), 4.00 (t, 2H), 5.15 (m, 2H), 6.40–6.55 (m, 3H), 7.00 (t, 2H), 7.20 (t, 1H), 7.35 (d, 1H), 7.40 (dd, 2H), 7.50 (s, 1H), 7.55 (d, 1H).

(S)1-[3-[[4-(1H-Indol-3-yl)butyl]methylamino]propyl]-1-(4-fluorophenyl)-1,3-dihydro-isobenzofuran-5carbonitrile (2d): LC/MS (m/z) 482 (MH$^+$), Rt=4.24, purity: 84%.

1-[3-[[4-(1H-Indol-3-yl)butyl]methylamino]propyl]1-phenyl-1,3-dihydroisobenzofuran (2e): LC/MS (m/z) 439 (MH), Rt=4.33, purity: 77%.

(S)-1-[3-[[3-(1H-Indol-3-yl)propyl]methylamino]propyl]-1-(4-fluorophenyl)-1,3-dihydroisobenzofuran-5-carbonitrile (21): LC/MS (m/z) 468 (MH$^+$), Rt=4.11, purity: >99%.

1-[3-[[3-(1H-Indol-3-yl)propyl]methylamino]propyl]-1-phenyl-1,3-dihydroisobenzofuran (2g): LC/MS (m/z) 425 (MH$^+$), Rt=4.15, purity: >99%.

5-[3-[[3-(1-Phenyl-1,3-dihydroisobenzofuran-1-yl)propyl]methylamino]propyl]-1,4-benzodioxane (2h): LC/MS (m/z) 444 (MH$^+$), Rt=4.12, purity: 97%.

5-[3-[[3-[1-(3-Chlorophenyl)-1,3-dihydroisobenzofuran-1-yl]propyl]methylamino]propyl]-1,4-benzodioxane (2i): LC/MS (m/z) 478 (MH$^+$), Rt=4.45, purity: 93%.

5-[3-[[3-[1-(4-Fluorophenyl)-1,3-dihydroisobenzofuran-1-yl]propyl]methylamino]propyl]-1,4benzodioxane (2j): LC/MS (m/z) 462 (MH$^+$), Rt=4.21, purity: 93%.

5-[3-[[3-[1-(3-Trifluoromethylphenyl)-1,3dihydroisobenzofuran-1-yl]propyl]methylamino]propyl]-1,4-benzodioxane (2k): LC/MS (m/z) 512 (MH$^+$), Rt=4.59, purity: 90%.

1-[3-[[3-(1,4-Benzodioxan-5-yl)propyl]methylamino]propyl]-1-(4chlorophenyl)-1,3-dihydroisobenzofuran-5-carbonitrile (2l): LC/MS (m/z) 503 (MH$^+$), Rt=4.59, purity: >99%.

1-[3-[4-(1H-Indol-4-yl)piperazinyl]propyl]-1-(4fluorophenyl)-1,3-dihydroisobenzofuran-5carbonitrile (2m): LC/MS (m/z) 481 (MH$^+$), Rt=5.61, purity: 97%.

1-[3-[4-(1H-Indol-5-yl)piperazinyl]propyl]-1-(4-fluorophenyl)-1,3-dihydroisobenzofuran-5-carbonitrile (2n): LC/MS (m/z) 481 (MH$^+$), Rt=5.69, purity: 94%.

1-[3-[4-(6-chloro-1H-Indol-3-yl)piperidinyl]propyl]-1-(4fluorophenyl)-1,3-dihydroisobenzofuran-5-carbonitrile (2o): LC/MS (m/z) 514 (MH$^+$), Rt=6.38, purity: 96%.

Example 3

5-[3-[[3-[5-Fluoro-1-(4-fluorophenyl)-1,3-dihydroisobenzofuran-1-yl]propyl]methylamino]propyl]-1,4-benzodioxane oxalate (3). A solution of 3-(1,4-benzodioxan-5-yl)propionic acid (0.8 g, 3.8 mmol), thionyl chloride (1 mL, 13.7 mmol) and one droplet of N,N-dimethylformamide in dichloromethane (30 mL) was boiled under reflux for 2 h. The volatile solvents were evaporated in vacuo and the remaining oil was dissolved in dichloromethane (30 mL). The resulting solution was added to a solution [3-[-5-fluoro-1-(4-fluorophenyl)-1,3-dihydroisobenzofuran-1-yl]propyl]methylamine (3.0 g, 10 mmol) and triethylamine (10 mL) in dichloromethane (100 mL). After stirring for 16 h the volatile solvents were evaporated in vacuo and the remaining oil was purified by column chromatography (ethyl acetate/heptane 75:25) affording 1.4 g of crude amide which was used without further purification.

To a solution of the amide (1.4 g, 2.8 mmol) in tetrahydrofuran (200 mL) was added lithium aluminum hydride (1.0 g, 2.6 mmol). After boiling of the resulting mixture under reflux for 3 h, the reaction mixture was cooled to 0° C. and carefully treated with water (1 mL) and 4N aqueous sodium hydroxide (1 mL). The resulting mixture was filtered and dried (Na$_2$SO$_4$). Evaporation of the volatile solvents afforded the title compound as an oil which was precipitated as its oxalate in acetone 0.9 g (19%): mp 131–33° C.; $^1$H NMR (DMSO-d$_6$) δ 1.35–1.45 (m, 1H), 1.45–1.55 (m, 1H), 1.75–1.80 (m, 2H), 2.10–2.25 (m, 2H), 2.50–2–55 (m, 2H), 2.60 ( s, 3H), 2.90 (t, 2H), 2.95 (t, 2H), 4.20–4.25 (m, 4H), 5.10 (m, 2H), 6.65–6.75 (m, 3H), 7.10–7.15 (m, 4H), 7.45–7.60 (m, 3H); MS m/z, 480 (MH+, 100), 225 (34), 109 (51).

Example 4

1-[3-[[2-(1H-Indol-3-yl)ethyl]methylamino]propyl]-1-(4-fluorophenyl)-1,3-dihydroisobenzofuran-5-carbonitrile (4a). To a suspension of acryl ester Wang resin (CH$_2$CHC(O)OR', HOR'=Wang resin) (loading 1.0 mmol/g) (300 mg, 0.30 mmol) (prepared from Wang resin (Loading 1.09 mmol/g, 200–400 mesh, 1% divinylbenzene) in analogy with the procedure described for the preparation of acryl ester hydroxymethyl polystyrene by Brown et al., J. Am. Chem. Soc., 1997, 119, 3288–95) in N,N-dimethylformamide (1.5 mL) was added a solution of 2-(1H-indolyl-3-yl)ethylamine (96 mg, 0.60 mmol) in N,N-dimethylformamide (1.5 mL). After stirring of the resulting suspension at room temperature for 16 h, the resin was filtered off and subsequently washed with 0.3M diisopropylethylamine in N,N-dimethylformamide (3×2.5 mL), methanol (2×2.5 mL) and dichloromethane (2×2.5 mL). To a suspension of the resulting resin in acetonitrile (1.5 mL) was added a solution of 1-(3-chloropropyl)-1-(4-fluorophenyl)-1,3-dihydroisobenzofuran-5-carbonitrile (9) (473 mg, 1.5 mmol) in acetonitrile (1.5 mL) and diisopropylethylamine (280 mL, 1.6 mmol). After heating of the resulting mixture at 75° C. under stirring for 16 h, the resin was filtered off. The resin was subsequently washed with acetonitrile (3×2.5 mL), methanol (3×2.5 mL), and dichloromethane (3×2.5 mL). The resin was suspended in N,N-dimethylformamide and diisopropylethylamine (280 mL, 1.6 mmol) and acetic anhydride (140 mL, 1.5 mmol) was added. After stirring of the resulting mixture for 16 h the resin was filtered off and washed with N,N-dimethylformamide (3×2.5 mL), methanol (3×2.5 mL), and dichloromethane (3×2.5 mL).

The intermediate resin was suspended in N,N-dimethylformamide (2 mL) and a solution of iodomethan (187 mL, 3.0 mmol) in N,N-dimethylformamide was added. After stirring of the resulting mixture for 16 h at room temperature, the resin was filtered off and washed with N,N-dimethylformamide (3×2.5 mL), methanol (3×2.5 mL), and dichloromethane (3×2.5 mL). To the resulting resin was added N,N-dimethylformamide (3.0 mL) and Diisopropylethylamine (165 mL, 0.94 mmol) and the mixture was stirred for 16 h. The resin was filtered off and washed with methanol (2×2.0 mL). The cleavage solution and the washing solutions were collected and the solvent evaporated in vacuo. The remaining oil was purified by ion exchange chromatography using an 6 mL Varian SCX column (1225–6011). The column was preconditioned with 10% acetic acid in methanol (3 mL) and the crude product was loaded on the column in a 2:1 mixture of methanol and 1-methyl-2-pyrrolidinone (3 mL). After the column was washed with methanol (18 mL) and acetonitrile (3 mL) the product was eluted from the column with 4N ammonia in methanol (4 mL) and subsequent evaporation of the solvents in vacuo afforded 13.9 mg (10%) of the title compound as an oil: LC/MS (m/z) 454 (MH$^+$), Rt=6.13 , purity: 98%.

The following compounds were prepared analogously:

1-(4-Fluorophenyl)-1-[3-[[2-(3-methoxyphenyl)ethyl]methylamino]propyl]-1,3-dihydroisobenzofuran-5-carbonitrile (4b): LC/MS (m/z) 445 (MH$^+$), R$_t$=8.58, purity: 88%

1-(4-Fluorophenyl)-1-[3-[[2-(3-methoxyphenyl)ethyl](prop-2-en-1-yl)amino]propyl]-1,3-dihydroisobenzofuran-5-carbonitrile (4c): $^1$H NMR (CDCl$_3$) δ 1.30–1.60 (m, 2H), 2.00–2.20 (m, 2H), 2.40–2.55 (m, 2H), 2.55–2.70 (m, 4H), 3.00–3.15 (broad s, 2 H), 3.80 (s, 3H), 5.05–5.20 (m, 4H), 5.75–5.85 (m, 1H), 6.65–6.80 (m, 3H), 7.00 (t, 2H), 7.20 (t, 1H), 7.30 (d, 1H), 7.40 (m, 2H), 7.50 (s, 1H), 7.60 (d, 1H); LC/MS (m/z) 471 (MH$^+$), R$_t$=8.85, purity: 91%

1-(4-Fluorophenyl)-1-[3-[[2-(2-methoxyphenyl)ethyl](prop-2-en-1-yl)amino]propyl]-1,3-dihydroisobenzofuran-5-carbonitrile (4d): $^1$H NMR (CDCl$_3$) δ 1.25–1.40 (m, 1H), 1.40–1.55 (m, 1H), 2.05–2.25 (m, 2H), 2.40–2.50 (m, 2H), 2.50–2.65 (m, 2H), 2.65–2.75 (m, 2H), 3.00–3.15 (m, 2H), 3.80 (s, 3H); 5.05–5.20 (m, 4H), 5.75–5.90 (m, 1H), 6.75–6.90 (m, 2H), 6.95–7.10 (m, 3H), 7.20 (t, 1H), 7.30 (d, 1H), 7.35–7.45 (m, 2H), 7.45 (s, 1H), 7.60 (d, 1H); LC/MS (m/z) 471 (MH$^+$), R$_t$=7.82, purity: >89%

1-[3-[[2-(2,5-Dimethoxyphenyl)ethyl]methylamino]propyl]-1-(4-fluorophenyl)-1,3-dihydroisobenzofuran-5-carbonitrile (4e): LC/MS (m/z) 475 (MH$^+$), R$_t$=8.68, purity: 94%

1-[3-[[2-(2,5-Dimethoxyphenyl)ethyl](prop-2-en-1-yl)amino]propyl]-1-(4-fluorophenyl)-1,3-dihydroisobenzofuran-5-carbonitrile (4f): LC/MS (m/z) 500 (MH$^+$), R$_t$=8.95, purity: 90%

1-(4-Fluorophenyl)-1-[3-[[2-phenoxyethyl]methylamino]propyl]-1,3-dihydroisobenzofuran-5carbonitrile (4g): LC/MS (m/z) 431 (MH$^+$), R$_t$=8.58, purity: 95%

1-[3-[[2-(1H-Indolyl-3-yl)ethyl](prop-2-en-1-yl)amino]propyl]-1-(4-fluorophenyl) 1,3-dihydroisobenzofuran-5carbonitrile (4h): LC/MS (m/z) 480 (MH$^+$), R$_t$=8.87, purity: 93%

1-(4-Fluorophenyl)-1-[3-[[2-phenoxyethyl](prop-2-en-1-yl)amino]propyl]-1,3-dihydroisobenzofuran-5carbonitrile (4i): LC/MS (m/z) 457 (MH$^+$), R$_t$=6.40, purity:>99%

1-(4Fluorophenyl)-1-[3-[[3-(2-methoxyphenyl)propyl]methylamino]propyl]-1,3-dihydroisobenzofuran-5-carbonitrile (4j): LC/MS (m/z) 459 (MH$^+$), R$_t$=6.43, purity:>99%

1-(4-Fluorophenyl)-1-[3-[[3-(2-methoxyphenyl)propyl](prop-2-en-1-yl)amino]propyl]-1,3-dihydroisobenzofuran-5-carbonitrile (4k): LC/MS (m/z) 485 (MH$^+$), R$_t$=6.77, purity: >99%

1-(4-Fluorophenyl)-1-[3-[[3-(3-methoxyphenyl)propyl](prop-2-en-1-yl)amino]propyl3-1,3-dihydroisobenzofuran-5-carbonitrile (4l): LC/MS (m/z) 485 (MH$^+$), R$_t$=6.63, purity: >99%

1-(4-Fluorophenyl)-1-[3-[[3-(2-methoxyphenoxy)propyl]methylaminopropyl]-1,3-dihydroisobenzofuran-5-carbonitrile (4m): LC/MS (m/z) 475 (MH$^+$), R$_t$=6.20, purity: >99%

1-(4-Fluorophenyl)-1-[3-[[3-(2-methoxyphenoxy)propyl](prop-2-en-1-yl)amino]propyl]-1,3-dihydroisobenzofuran-5-carbonitrile (4n): LC/MS (m/z) 501 (MH$^+$), R$_t$=6.50, purity: >99%

1-(4-Fluorophenyl)-1-[3-[[3-(3-methoxyphenoxy)propyl]methylamino]propyl]-1,3-dihydroisobenzofuran-5-carbonitrile (4o): LC/MS (m/z) 475 (MH$^+$), R$_t$=6.35, purity: >99%

1-(4-Fluorophenyl)-1-[3-[[3-(3-methoxyphenoxy)propyl3(prop-2-en-1-yl)amino]propyl]-1,3-dihydroisobenzofuran-5-carbonitrile (4p): LC/MS (m/z) 501 (MH$^+$), R$_t$=6.65, purity: >99%

1-[3-[(2-Benzyloxyethyl)methylamino]propyl]-1-(4-fluorophenyl)-1,3-dihydroisobenzofuran-5-carbonitrile (4q): LC/MS (m/z) 445 (MH$^+$), R$_t$=6.18 , purity: 98%

1-[3-[(2-Benzyloxyethyl)(prop-2-en-1-yl)amino]propyl]-1-(4-fluorophenyl)-1,3-dihydroisobenzofuran-5-carbonitrile (4r): LC/MS (m/z) 471 (MH$^+$), R$_t$=6.55, purity: 97%

1-[3-[[3-(1H-Indol-3-yl)propyl]methylamino]propyl]-1-(4-fluorophenyl)-1,3-dihydroisobenzofuran-5-carbonitrile (4s): LC/MS (m/z) 468 (MH$^+$), R$_t$=6.28, purity:80%

1-[3-[[3-(1H-Indol-3-yl)propyl](prop-2-en-1-yl)amino]propyl]-1-(4-fluorophenyl)-1,3-dihydroisobenzofuran-5-carbonitrile (4t): LC/MS (m/z) 494 (MH$^+$), R$_t$=6.60, purity: 82%

1-[3-[[3-(1H-Indol-3-yl)propyl](prop-2-yl-1-yl)amino]propyl]-1-(4-fluorophenyl)-1,3-dihydroisobenzofuran-5-carbonitrile (4u): LC/MS (m/z) 492 (MH$^+$), R$_t$=6.59, purity:73%

Example 5

5-hydroxymethyl-1,4-benzodioxan (5). To a suspension of lithium aluminum hydride (7.0 g, 0.18 mmol) in dry diethyl ether (100 mL) was added a solution of ethyl 1,4-benzodioxan-5-carboxylate (35 g, 0.17 mmol) in diethyl ether (100 mL). After boiling under reflux for 2 h, the reaction mixture was cooled to 0° C. and carefully treated with water (35 mL) and 4N aqueous sodium hydroxide (35 mL). The resulting mixture was filtered and dried (Na$_2$SO$_4$). Evaporation of the solvents afforded 25 g (88%) crystalline title compound: mp 51–53° C.; $^1$H NMR (CDCl$_3$) δ 2.50 (s, 1H), 4.20–4.3 (m, 4H), 4.60 (s, 2H), 6.75–6.90 (m, 3H).

Example 6

2-(1,4-benzodioxan-5-yl)acetic acid (6). To a solution of 5-hydroxymethyl-1,4-benzodioxan (8.0 g, 48 mmol) in dichloromethane (200 mL) was added two droplets of N,N-dimethylformamide and thionyl chloride (5.0 mL, 68 mmol) at room temperature. After the resulting solution was boiled under reflux for 1 h and subsequently cooled to room temperature water (100 mL) was added. The phases were separated and the organic phase was dried (MgSO$_4$) and the solvents evaporated in vacuo. A solution of the remaining oil (8.5 g, 46 mmol) was added to a mixture of sodium cyanide (5.0 g, 102 mmol) and N,N-dimethylformamide (100 mL) at room temperature. After stirring for 16 h at room temperature ice was added and the resulting slurry was extracted with diethyl ether (2×250 mL). The collected organic phases were washed with saturated calcium chloride, dried (Na$_2$SO$_4$) and the solvents were evaporated in vacuo. A mixture of the remaining oil (6.0 g, 34 mmol), ethanol (200 mL), sodium hydroxide (6.0 g) and water (6 mL) was boiled under reflux for 16 h. After evaporation of the solvents in vacuo, water (200 mL) was added and the resulting slurry was extracted with diethyl ether (2×200 mL). The collected organic phases were washed with brine, dried (Na$_2$SO$_4$) and the solvents were evaporated in vacuo affording 4.0 g (43%) of the title compound as an oil: $^1$H NMR (CDCl$_3$) δ 3.65 (s, 2H), 4.15–4.30 (m, 4H), 6.70–6.85 (m, 3H).

Example 7

5-(2-bromoethyl)-1,4-benzodioxan (7a). To a solution of 2-(1,4-benzodioxan-5-yl)acetic acid (6) (4.0 g, 21 mmol) in tetrahydrofuran (200 mL) was added lithium aluminum hydride (1.0 g, 26 mmol). After boiling under reflux for 2 h the reaction mixture was cooled to 0° C. and carefully treated with water (1 mL) and 4N aqueous sodium hydroxide (1 mL). The resulting mixture was filtered and dried ($Na_2SO_4$). Evaporation of the solvents afforded crude intermediate alcohol (3.9 g, 21 mmol) as an oil which was used without further purification. To a solution of the intermediate alcohol and tetrabromomethane (8.8 g, 27 mmol) in acetonitrile (120 mL) was added triphenylphosphine (6.3 g, 24.9 mmol) in small portions at 0° C. After reaction for further 15 minutes at 0° C. the solvents were evaporated in vacuo and the remaining oil was purified by column chromatography (ethyl acetate/heptane 66:34) affording 5.5 g (99%) of the title compound as an oil: $^1H$ NMR ($CDCl_3$) δ 3.15 (t, 2H), 3.55 (t, 2H), 4.204.35 (m, 4H), 6.65–6.85 (m, 3H).

The following compounds were prepared analogously:

5-(3-Bromopropyl)-1,4-benzodioxan (7b): (oil) $^1H$ NMR ($CDCl_3$) δ 2.15 (qui, 2H), 2.75 (t, 2H), 3.40 (t, 2H), 4.20–4.30 (m, 4H), 6.656.75 (m, 3H).

5-4Bromobutyl)-1,4-benzodioxan (7c): (oil) $^1H$ NMR ($CDCl_3$) δ 1.70–1.80 (qui, 2H), 1.85–1.90 (qui, 2H), 2.60 (t, 2H), 3.40 (t, 2H), 4.25 (m, 4H), 6.65–6.75 (m, 3H).

1-2-Bromoethoxy)-2-methoxybenzene (7d): (oil) $^1H$ NMR ($CDCl_3$) δ 3.65 (t, 2H), 3.85 (s, 3H), 4.30 (t, 2H), 6.80–7.05 (m, 4H).

1-(2-Bromoethoxy)-3-methoxybenzene (7e): (oil) $^1H$ NMR ($CDCl_3$) δ 3.60 (t, 2H), 3.80 (s, 3H), 4.25 (t, 2H), 6.45–6.55 (m, 3H), 7.15 (t, 1H).

Example 8

4-(1,4-Benzodioxan-5-yl)butanoic acid (8a). Neat 5-(4-bromoethyl)-1,4-benzodioxan (7c) (18.0 g, 74 mmol) was added to a mixture of diethyl malonate (12 g, 75 mmol), potassium tert-butoxide (8.4 g, 75 mmol), toluene (250 mL) and dimethyl sulfoxide (50 mL) at room temperature. The resulting mixture was heated at 50° C. for 3 h, cooled to room temperature and water was added. After the slurry was acidified with concentrated hydrochloric acid the phases were separated. The organic phase was dried ($Na_2SO_4$) and the solvents evaporated in vacuo. The remaining oil was dissolved in ethanol (200 mL) and 9N aqueous sodium hydroxide. After boiling of the resulting mixture under reflux for 15 minutes the solution was stirred at room temperature for 1 h. The solvents were evaporated and the remaining oil was diluted in water (200 mL) and extracted with diethyl ether (2×100 mL). The aqueous phase was acidified with 4N hydrochloric acid and extracted with ethyl acetate (2×200 mL). Drying of the collected organic phases and evaporation of the solvents in vacuo afforded the intermediate dicarboxylic acid as an oil (5.0 g). The crude oil was diluted in pyridine (10 mL) and the resulting solution was heated at 115° C. for 1 h. After cooling to room temperature, water (50 mL) was added and the aqueous phase was acidified with 4N hydrochloric acid. The resulting slurry was extracted with diethyl ether (2×50 mL) and the collected organic phases were dried ($Na_2SO_4$). Evaporation of the solvents in vacuo afforded 3.8 g (23%) of the title compound as an oil.

The following compound was prepared analogously:

3-(1,4Benzodioxan-5-yl)propionic acid (8b): (oil) $^1H$ NMR ($CDCl_3$) δ 2.65 (t, 2H), 2.95 (t, 2H), 4.20–4.30 (m, 4H), 6.65–6.80 (m, 3H).

Example 9

1-(3-Chloropropyl)-1-4-fluorophenyl)-1,3-dihydroisobenzofuran-5 carbonitrile (9). To a mixture of 1-[3methylamino)propyl]-1-4fluorophenyl)-1,3-dihydroisobenzofuran-5-carbonitrile (43 g, 138 mmol), potassium carbonate (30 g, 217 mmol), and ethanol (400 mL) was added ethyl bromoacetate (20 mL, 180 mmol) at room temperature and the resulting mixture was boiled under reflux for 90 minutes. After cooling to room temperature water (800 mL) and ethyl acetate (500 mL) was added and the phases were separated. The organic phase was washed with brine, dried ($Na_2SO_4$) and the solvents evaporated in vacuo. The remaining oil (36 g, 101 mmol) was added slowly to a mixture of ethyl chloroformate (50 mL, 523 mmol), potassium carbonate (36 g, 260) and toluene (300 mL) at 90° C. After boiling of the resulting mixture under reflux for 1 h and cooling to room temperature, the solvents were evaporated in vacuo. The remaining oil was purified by column chromatography (ethyl acetate/heptane 1:3) giving 15 g (34%) of the title compound as an oil: $^1H$ NMR ($CDCl_3$) δ 1.60–1.90 (m, 2H), 2.20–2.45 (m, 21), 3.45–3.55 (m, 2H), 5.20 (m, 2H), 6.95–7.10 (t, 2H), 7.40–7.55 (m, 4H), 7.60 (d, 1H).

Example 10

[2-(2-Methoxyphenoxy)ethyl]methylamine (10a). A solution of 1-(2-bromoethoxy)-2-methoxybenzene (7d) (7.7 g, 33 mmol) in a 33% solution of methylamine in ethanol was heated at 80° C. in a sealed tube for 16 h. After cooling to room temperature, the solvents were evaporated in vacuo. A 2N aqueous solution of sodium hydroxide was added to the remaining oil and the resulting slurry was extracted with ethyl acetate (2×250 mL). The collected organic phases were dried ($Na_2SO_4$) and the solvents evaporated in vacuo giving 5.9 g (98%) of the title compound as an oil: $^1H$ NMR ($CDCl_3$) δ 1.85 (broad s, 1H), 2.50 (s, 3H), 3.00 (t, 2H), 3.85 (s, 3H), 4.10 (t, 2H), 6.85–6.95 (m, 4H).

The following compound was prepared analogously:

[2-(3-Methoxyphenoxy)ethyl]methylamine (10b): (oil) $^1H$ NMR ($CDCl_3$) δ 1.85 (broad s, 1H), 2.50 (s, 3H), 2.95 (t, 2H), 3.80 (s, 3H), 4.05 (t, 2H), 6.45–6.55 (m, 3H), 7.15 (t, 1H).

Example 11

2-(4Chlorobutyl)-dioxolan-4-ylmethoxymethyl polystyrene (11a). A 2 L round bottom flask was charged with 2,2-dimethyldioxolan-4-ylmethoxymethyl polystyrene (90 g, 72 mmol, commercially available as (±)-1-(2,3-isopropylidene) glycerol polystyrene from Calbiochem-Novabiochem, cat. no. 01-64-0291). Toluene (900 mL) followed by p-toluenesulfonic acid mono hydrate (5.0 g, 26 mmol), sodium sulfate (25 g), and readily available 5-chloropentanal (25.5 g, 211 mmol) were added and the mixture heated at reflux for 12 h. The reflux condenser was replaced by a Dean-Stark apparatus and the mixture was heated at reflux for an additional 3 h. After cooling of the reaction mixture to 60° C., the resin was filtered and washed with toluene (200 mL), tetrahydrofuran/pyridine (1:1, 200 mL), tetrahydrofuran/water/pyridine (10:10:1, 200 mL), methanol (200 mL), water (200 mL), tetrahydrofuran (200 mL), dichloromethane (200 mL), methanol (3×200 mL), and dichloromethane (3×200 mL). The resin was dried in vacuo (55° C., 12 h) to yield the title compound 11a (97 g).

The following compounds were prepared analogously:

2-(3-Chloropropyl)-dioxolan-4-ylmethoxymethyl polystyrene (11b)

2-(5-Chloropentyl)-dioxolan-4-ylmethoxymethyl polystyrene (11c)

Example 12

1-[3-[[3-(1H-Indol-3-yl)propyl]methylamino]propyl]-1-(4-fluorophenyl) 1,3-dihydroisobenzofuran-5-carbonitrile (4s). 2-(4-Chlorobutyl)-dioxolan-4-ylmethoxymethyl polystyrene (11a) (8.0 g, 6.1 mmol) was suspended in dry N,N-dimethylformamide (90 mL). Sodium iodide (3.38 g, 22.5 mmol) was added followed by diisopropylethylamine (6.30 mL, 36 mmol) and 1-[3-(methylamino)propyl]-1-(4fluorophenyl)-1,3-dihydroisobenzofuran-5-carbonitrile (5.56 g, 18 mmol). The reaction mixture was heated at 80° C. under stirring for 12 h. After cooling to room temperature, the resin was filtered and washed with with N,N-dimethylformamide (3×65 mL), methanol (3×60 mL), tetrahydrofuran (3×60 mL), and then subsequently with methanol and tetrahydrofuran (each approximately 40 mL, 5 cycles). Finally, the resin was washed with tetrahydrofuran (4×40 mL) and dried in vacuo (55° C., 12 h, 9.5 g).

An aliquot of this material (147 mg, 0.112 mmol) and phenylhydrazine hydrochloride (43 mg, 0.297 mmol) were mixed in a reactor tube. A 0.5M solution of anhydrous zinc chloride in acetic acid (1.5 mL) was added and the reaction tube was sealed. The reaction mixture was stirred for 12 h at 75° C. After cooling to room temperature, the reaction mixture was filtered and the residual resin washed with dimethylsulfoxide (1.5 mL). To the combined filtrates was added saturated aqueous sodium bicarbonate solution (1.5 mL). The solution was loaded on a reversed solid phase extraction column (C-18, 1 g, Varian Mega Bond Elut®, Chrompack cat. no. 220508), pre-conditioned with methanol (3 mL) and water (3 mL). The column was washed with water (4 mL) and the product was eluted with methanol (4.5 mL). The resulting solution was loaded on an ion exchange column (SCX, 1 g, Varian Mega Bond Elut®, Chrompack cat. no. 220776), pre-conditioned with 10% solution of acetic acid in methanol (3 mL) and the column was washed with methanol (4 mL) and acetonitrile (4 mL), followed by elution with 4N solution of ammonia in methanol (4.5 mL). Evaporation of the volatile solvents afforded the title compound (4s) as a colourless oil (22 mg, 42%). LC/MS (m/z) 468 (MH$^+$), Rt=4.30, purity: 83%.

The following compounds were prepared analogously:

1-[3-[[2-(5-Methyl-1H-indol-3-yl)ethyl]methylamino]propyl]-1-(4-fluorophenyl)-1,3-dihydroisobenzofuran-5-carbonitrile (12a): LC/MS (m/z) 468 (MH$^+$), Rt=4.22, purity: 96%.

1-[3-[[2-(7-Fluoro-1H-indol-3-yl)ethyl]methylamino]propyl]-1-(4-fluorophenyl)-1,3-dihydroisobenzofuran-5-carbonitrile (12b): $^1$H NMR (CDCl$_3$) δ 1.2–1.4 (m, 1H), 1.4–1.55 (m,1H), 2.0–2.25 (m, 2H), 2.25 (s, 3H), 2.39 (t, 2H), 2.60 (t, 2H), 2.86 (t, 2H), 5.05–5.21 (m, 2H), 6.93–7.07 (m, 4H), 7.17–7.3 (m, 2H), 7.3–7.4 (m, 3H), 7.4–7.5 (m, 1H), 7.5–7.6 (m, 1H); LC/MS (m/z) 472 (MH$^+$), Rt=4.12, purity: 86%.

5-Fluoro-1-[3-[[3-(5-methyl-1H-indol-3-yl)propyl]methylamino]propyl]-1-(4-fluorophenyl)-1,3-dihydroisobenzofuran (12c): LC/MS (m/z) 475 (MH$^+$), Rt=4.57, purity: 92%.

5-Fluoro-1-[3-[[3-(7-fluoro-1H-indol-3-yl)propyl]methylamino]propyl]-1-(4-fluorophenyl)-1,3dihydroisobenzofuran (12d): LC/MS (m/z) 479 (MH$^+$), Rt=4.47, purity: 94%.

1-[3-[[3-(5-Methyl-1H-indol-3-yl)propyl]methylamino]propyl]-1-(4-fluorophenyl)-1,3-dihydroisobenzofuran-5-carbonitrile (12e): LC/MS (m/z) 482 (MH$^+$), Rt=4.54, purity: 80%.

1-[3-Ethyl[3-(1H-indol-3-yl)propyl]amino]propyl]-1-(4-fluorophenyl)-1,3-dihydroisobenzofuran-5-carbonitrile (12f): LC/MS (m/z) 482 (MH$^+$), Rt=4.31, purity: 94%.

1-[3-[Ethyl[2-(5-methyl-1H-indol-3-yl)ethyl]amino]propyl-1-(4-fluorophenyl)-1,3-dihydroisobenzofuran-5-carbonitrile (12g): LC/MS (m/z) 482 (MH$^+$), Rt=4.38, purity: 89%.

1-[3-[[3-(7-Fluoro-1H-indol-3-yl)propyl]methylamino]propyl]-1-(4-fluorophenyl)-1,3-dihydroisobenzofuran-5-carbonitrile (12h): LC/MS (m/z) 486 (MH$^+$), Rt=4.16, purity: 79%.

1-[3-[[3-(5-Fluoro-1H-indol-3-yl)propyl]methylamino]propyl]-1-(4-fluorophenyl)-1,3-dihydroisobenzofuran-5-carbonitrile (12i): $^1$H NMR (CDCl$_3$) δ 1.23–1.39 (m, 1H), 1.39–1.54 (m, 1H), 1.80 (tt, 2H), 2.06–2.24 (m, 5H), 2.30 (t, 2H), 2.34 (t, 2H), 2.68 (t, 2H), 5.13 (d, 1H), 5.17 (d, 1H), 6.93 (dt, 2H), 6.99 (t, 2H), 7.21 (dd, 1H), 7.23–7.29 (m, 1H), 7.33 (d, 1H), 7.40 (dd, 2H), 7.47 (s, 1H), 7.55 (d, 1H), 8.01 (s, 1H); LC/MS (m/z) 486 (MH$^+$), Rt=4.12, purity: 98%.

1-[3-[Ethyl[2-(5-fluoro-1H-indol-3-yl)ethyl]amino]propyl]-1-(4fluorophenyl)-1,3-dihydroisobenzofuran-5-carbonitrile (12j): $^1$H NMR (CDCl$_3$) δ 1.02 (t, 3H), 1.25–1.38 (m, 1H), 1.42–1.54 (m, 1H), 2.10 (ddd, 1H), 2.18 (ddd, 1H), 2.49 (t, 2H), 2.56 (q, 2H), 2.61–2.70 (m, 2H), 2.74–2.82 (m, 2H), 5.13 (d, 1H), 5.18 (d, 1H), 6.94 (dt, 2H), 6.99 (t, 2H), 7.19 (dd, 1H), 7.23–7.30 (m, 2H), 7.38 (dd, 2H), 7.47 (s, 1H), 7.54 (d, 1H), 8.01 (s, 1H); LC/MS (m/z) 486 (MH$^+$), Rt=4.24, purity: 95%.

1-[3-[Ethyl[2-(7-fluoro-1H-indol-3-yl)ethylamino]propyl]-1-(4fluorophenyl)-1,3-dihydroisobenzofuran-5-carbonitrile (12k): $^1$H NMR (CDCl$_3$) δ 1.02 (t, 3H), 1.22–1.37 (m, 1H), 1.42–1.53 (m,1H), 2.0–2.2 (m, 2E), 2.36–2.6 (m, 4H), 2.67 (t, 2H), 2.81 (t, 2H), 5.12 (dd, 1H), 5.16 (d, 1H), 6.86–7.06 (m, 4H), 7.2–7.4 (m, 5H), 7.46 (d, 1H), 7.54 (d, 1H); LC/MS (m/z) 486 (MH$^+$), Rt=4.26, purity: 91%.

1-[3-[[2-(5-Chloro-1H-indol-3-yl)ethyl]methylamino]propyl]-1-(4-fluorophenyl) 1,3-dihydroisobenzofuran-5-carbonitrile (12l): LC/MS (m/z) 488 (MH$^+$), Rt=4.30, purity: 85%.

1-[3-[[3-(5-Chloro-1H-indol-3-yl)propyl]methylamino]propyl]-5-fluoro-1-(4-fluorophenyl)-1,3-dihydroisobenzofuran (12m): LC/MS (m/z) 495 (MH$^+$), Rt=4.64, purity: 94%.

1-[3-[[4-(5-Methyl-1H-indol-3-yl)butyl]methylamino]propyl]-1-(4-fluorophenyl)-1,3-dihydroisobenzofuran-5-carbonitrile (12n): LC/MS (m/z) 496 (MH$^+$), Rt=4.50, purity: 78%.

1-[3-[Ethyl[3-(5-methyl-1H-indol-3-yl)propyl]amino]propyl]-1-(4-fluorophenyl)-1,3-dihydroisobenzofuran-5-carbonitrile (12o): LC/MS (m/z) 496 (MH$^+$), Rt=4.50, purity: 92%.

1-[3-[Ethyl[3-(7-fluoro-1H-indol-3-yl)propyl]amino]propyl]-1-(4-fluorophenyl)-1,3-dihydroisobenzofuran-5carbonitrile (12p): LC/MS (m/z) 500 (MH$^+$), Rt=4.39, purity: 91%.

1-[3-[Ethyl[3-(5-fluoro-1H-indol-3-yl)propyl]amino]propyl]-1-(4-fluorophenyl)-1,3-dihydroisobenzofuran-5carbonitrile (12q): $^1$H NMR (CDCl$_3$) δ 0.95 (t, 3H), 1.21–1.36 (m, 1H), 1.36–1.50 (m, 1H), 1.77 (tt, 2H), 2.10 (ddd,1H), 2.18 (ddd, 1H), 2.34–2.50 (m, 6H), 2.65 (t, 2H), 5.12 (d, 1H), 5.15 (d, 1H), 6.90–7.04 (m, 4H), 7.20 (dd, 1H), 7.25 (dd, 1H), 7.30 (d, 1H), 7.36 (m, 2H), 7.45 (s, 1H), 7.52 (d, 1H), 8.12 (s, 1H); LC/MS (m/z) 500 (MH$^+$), Rt=4.35, purity: 94%.

1-[3-[[3-(5-Chloro-1H-indol-3-yl)propyl]methylamino]propyl]-1-(4-fluorophenyl)-1,3-dihydroisobenzofuran-5-carbonitrile (12r): LC/MS (m/z) 502 (MH$^+$), Rt=4.55, purity: 91%.

1-[3-[[2-(7-Chloro-1H-indol-3-yl)ethyl]ethylamino]propyl]-1-(4-fluorophenyl)-1,3-dihydroisobenzofuran-5-carbonitrile (12s): LC/MS (m/z) 502 (MH$^+$), Rt=4.41, purity: 80%.

1-[3-[[2-(5-Chloro-1H-indol-3-yl)ethyl]ethylamino]propyl]-1-(4-fluorophenyl)-1,3-dihydroisobenzofuran-5-carbonitrile (12t): LC/MS (m/z) 502 (MH$^+$), Rt=4.44, purity: 95%.

1-[3-[[2-(5,7-Difluoro-1H-indol-3-yl)ethyl]ethylamino]propyl]-1-(4-fluorophenyl)-1,3-dihydroisobenzofuran-5-carbonitrile (12u): LC/MS (m/z) 504 (MH$^+$), Rt=4.35, purity: 92%.

1-[3-[[4-(5-Fluoro-1H-indol-3-yl)butyl]ethylamino]propyl]-1-(4-fluorophenyl)-1,3-dihydroisobenzofuran-5-carbonitrile (12v): LC/MS (m/z) 514 (MH$^+$), Rt=4.50, purity: 91%.

1-[3-[[4-(5-Chloro-1H-indol-3-yl)butyl]methylamino]propyl]-1-(4-fluorophenyl)-1,3-dihydroisobenzofuran-5-carbonitrile (12w): LC/MS (m/z) 516 (MH$^+$), Rt=4.59, purity: 90%.

1-[3-[[3-(5-Chloro-1H-indol-3-yl)propyl]ethylamino]propyl]-1-(4-fluorophenyl)-1,3-dihydroisobenzofuran-5-carbonitrile (12x): LC/MS (m/z) 516 (MH$^+$), Rt=4.56, purity: 97%.

1-[3-[[3-(5,7-Difluoro-1H-indol-3-yl)propyl]ethylamino]propyl]-1-(4-fluorophenyl)-1,3-dihydroisobenzofuran-5-carbonitrile (12y): LC/MS (m/z) 518 (MH$^+$), Rt=4.47, purity: 90%.

1-[3-[[2-(5-Bromo-1H-indol-3-yl)ethyl]methylamino]propyl]-1-(4-fluorophenyl)-1,3-dihydroisobenzofuran-5-carbonitrile (12z): LC/MS (m/z) 532 (MH$^+$), Rt=4.46, purity: 87%.

1-[3-[[3-(5-Bromo-1H-indol-3-yl)propyl]methylamino]propyl]-1-(4-fluorophenyl)-1,3-dihydroisobenzofuran-5-carbonitrile (12aa): LC/MS (m/z) 546 (MH$^+$), Rt=4.59, purity: 88%.

1-[3-[[2-(5-Bromo-1H-indol-3-yl)ethyl]ethylamino]propyl]-1-(4-fluorophenyl)-1,3-dihydroisobenzofuran-5-carbonitrile (12ab): LC/MS (m/z) 546 (MH$^+$), Rt=4.50, purity: 90%.

1-[3-[[4(5-Bromo-1H-indol-3-yl)butyl]methylamino]propyl]-1-(4-fluorophenyl)-1,3-dihydroisobenzofuran-5-carbonitrile (12ac): LC/MS (m/z) 560 (MH$^+$), Rt=4.61, purity: 90%.

1-(3-[[3-(5-Bromo-1H-indol-3-yl)propyl]ethylamino]propyl]-1-(4fluorophenyl)-1,3-dihydroisobenzofuran-5-carbonitrile (12ad): LC/MS (m/z) 560 (MH$^+$), Rt=4.62, purity: 92%.

1-[3-[Ethyl[2-(5-iodo-1H-indol-3-yl)ethylaminopropyl]-1-(4-fluorophenyl)-1,3-dihydroisobenzofuran-5-carbonitrile (12ae): LC/MS (m/z) 594 (MH$^+$), Rt=4.60, purity: 82%.

1-[3-[Ethyl[3-(5-iodo-1H-indol-3-yl)propyl]amino]propyl]-1-(4-fluorophenyl)-1,3-dihydroisobenzofuran-5-carbonitrile (12af): LC/MS (m/z) 608 (MH$^+$), Rt=4.72, purity: 71%.

1-[2-[[4-(5-Chloro-1H-indol-3-yl)butyl]methylamino]ethyl]-1-(4-fluorophenyl)-1,3-dihydroisobenzofuran-5-carbonitrile (12ag): LC/MS (m/z) 502 (MH$^+$), Rt=4.50, purity: 90%.

1-[2-[[4-(5-Bromo-1H-indol-3-yl)butyl]methylamino]ethyl]-1-(4-fluorophenyl)-1,3-dihydroisobenzofuran-5-carbonitrile (12ah): LC/MS (m/z) 546 (MH$^+$), Rt=4.55, purity: 83%.

1-[4-[[2-(5,7-Difluoro-1H-indol-3-yl)ethyl]methylaminobutyl]-1-(4-fluorophenyl)-1,3-dihydroisobenzofuran-5-carbonitrile (12ai): LC/MS (m/z) 504 (MH$^+$), Rt=4.36, purity: 87%.

1-[4-[[2-(7-Chloro-1H-indol-3-yl)ethyl]methylamino]butyl]-1-(4-fluorophenyl)-1,3-dihydroisobenzofuran-5-carbonitrile (12aj): LC/MS (m/z) 502 (MH$^+$), Rt=4.42, purity: 70%.

1-[4-[[2-(5-Chloro-1H-indol-3-yl)ethyl]methylamino]butyl]-1-(4-fluorophenyl)-1,3-dihydroisobenzofuran-5-carbonitrile (12ak): LC/MS (m/z) 502 (MH$^+$), Rt=4.45, purity: 91%

1-[4-[[2-(5-Bromo-1H-indol-3-yl)ethyl]methylamino]butyl]-1-(4-fluorophenyl)-1,3-dihydroisobenzofuran-5-carbonitrile (12al): LC/MS (m/z) 546 (MH$^+$), Rt=4.48, purity: 90%.

1-[4-[[2-(5-Methyl-1H-indol-3-yl)ethyl]methylamino]butyl-1-(4-fluorophenyl)-1,3-dihydroisobenzofuran-5-carbonitrile (12am): LC/MS (m/z) 482 (MH$^+$), Rt=4.37, purity: 87%.

1-[4-[[2-(5-Iodo-1H-indol-3-yl)ethyl]methylamino]butyl]-1(4-fluorophenyl)-1,3-dihydroisobenzofuran-5carbonitrile (12an): LC/MS (m/z) 594 (MH$^+$), Rt=4.57, purity: 83%.

1-[4-[[2-(5-(2-methyl-2-propyl)-1H-indol-3-yl)ethyl]methylamino]butyl]-1-(4-fluorophenyl)-1,3-dihydroisobenzofuran-5-carbonitrile (12ao): LC/MS (m/z) 524 (MH$^+$), Rt=4.85, purity: 91%.

1-[4-[[2-(5-(2-Propyl)-1H-indol-3-yl)ethyl]methylamino]butyl]-1-(4-fluorophenyl)-1,3-dihydroisobenzofuran-5-carbonitrile (12ap): LC/MS (m/z) 510 (MH$^+$), Rt=4.72, purity: 92%.

Example 13

1-[3-[[2-(5-Methyl-1H-indol-3-yl)ethyl](prop-2-en-1-yl)amino]propyl]-1-(4-fluorophenyl)-1,3-dihydroisobenzofuran-5-carbonitrile (13a). 2-(3-Chloropropyl)-1,3-dioxolan4-ylmethoxymethyl polystyrene (2.0 g, 1.6 mmol) was suspended in dry N,N-dimethylformamide (15 mL). Sodium iodide (0.67 g, 4.5 mmol) was added followed by diisopropylethylamine (1.70 mL, 9.6 mmol) and alkyl amine (0.28 g, 4.8 mmol). The reaction mixture was heated at 80° C. under stirring for 12 h. After cooling to room temperature, the resin was filtered and washed with N,N-dimethylformamide (3×15 mL), methanol (3×15 mL), tetrahydrofuran (3×15 mL), and subsequently with methanol and tetrahydrofuran (each 10 mL, 5 cycles). Finally, the resin was washed with tetrahydrofuran (4×10 mL) and dried in vacuo (55° C., 12 h). The resin was then suspended in dry N,N-dimethylformamide (20 mL). Sodium iodide (0.60 g, 4.0 mmol) was added followed by diisopropylethylamine (0.48 mL, 2.7 mmol) and 1-(3-chloropropyl)-1-(4-fluorophenyl)-1,3-dihydroisobenzofuran-5-carbonitrile (9) (0.79 g, 2.5 mmol). The reaction mixture was stirred for 12 h at 80° C. After cooling to room temperature, the resin was filtered and washed with with N,N-dimethylformamide (3×15 mL), methanol (3×15 mL), tetrahydrofuran (3×15 mL), and then subsequently with methanol and tetrahydrofuran (each ca 15 mL, 5 cycles). Finally, the resin was washed with tetrahydrofuran (4×15 mL) and dried in vacuo (55° C., 12 h, 2.1 g).

An aliquot of this material (120 mg, ca 0.08 mmol) and 4-methylphenylhydrazine hydrochloride (ca 40 mg, 0.20 mmol) were mixed in a reactor tube. A 0.5M solution of anhydrous zinc chloride in acetic acid (1.5 mL) was added and the reaction tube was sealed. The reaction mixture was stirred for 12 h at 75° C. After cooling to room temperature, the reaction mixture was filtered and the residual resin washed with dimethylsulfoxide (1.5 mL). To the combined filtrates was added saturated aqueous sodium bicarbonate solution (1.5 mL). The solution was loaded on a reversed phase column (C-18, 1 g, Varian Mega Bond Elut®, Chrompack cat. no. 220508), pre-conditioned with methanol (3 mL) and water (3 mL). The column was washed with water (4 mL) and the product was eluted with methanol (4.5 mL). After evaporation of the volatile solvents, the crude product was purified by preparative reversed phase HPLC chromatography. The resulting solution was loaded on an ion exchange column (SCX, 1 g, Varian Mega Bond Elut®, Chrompack cat. no. 220776), pre-conditioned with 10% solution of acetic acid in methanol (3 mL) and the column was washed with methanol (4 mL) and acetonitrile (4 mL), followed by elution with 4N solution of ammonia in methanol (4.5 mL). Evaporation of the volatile solvents afforded the title compound (13a) as a colorless oil (2 mg, 4 μmol, 5%). LC/MS (m/z) 494 (MH$^+$), Rt=4.44, purity: 93%.

The following compounds were prepared analogously:

1-[3-[[2-(5-Fluoro-1H-indol-3-yl)ethyl](prop-2-en-1-yl)amino]propyl]-1-(4-fluorophenyl)-1,3-dihydroisobenzofuran-5-carbonitrile (13b): LC/MS (m/z) 498 (MH$^+$), Rt=4.31, purity: 96%.

1-[3-[[2-(7-Fluoro-1H-indol-3-yl)ethyl](prop-2-en-1-yl)amino]propyl]-1-(4-fluorophenyl)-1,3-dihydroisobenzofuran-5-carbonitrile (13c): LC/MS (m/z) 498 (MH$^+$), Rt=4.34, purity: 86%.

1-[3-[[3-(5-Fluoro-1H-indol-3-yl)propyl](prop-2-en-1-yl)amino]propyl]-1-(4-fluorophenyl)-1,3-dihydroisobenzofuran-5-carbonitrile (13d): LC/MS (m/z) 512 (MH$^+$), Rt=4.48, purity: 96%.

1-[3-[[3-(7-Fluoro-1H-indol-3-yl)propyl](prop-2-en-1-yl)amino]propyl]-1-(4-fluorophenyl)-1,3-dihydroisobenzofuran-5-carbonitrile (13e): LC/MS (m/z) 512 (MH$^+$), Rt=4.49, purity: 78%.

1-[3-[[2-5-Chloro-1H-indol-3-yl)ethyl](prop-2-en-1-yl)amino]propyl]-1-(4-fluorophenyl)-1,3-dihydroisobenzofuran-5-carbonitrile (13f): LC/MS (m/z) 514 (MH$^+$), Rt=4.52, purity: 86%.

1-[3-[[2-(5,7-Difluoro-1H-indol-3-yl)ethyl]propylamino]propyl]-1-(4-fluorophenyl)-1,3-dihydroisobenzofuran-5-carbonitrile (13g): LC/MS (m/z) 518 (MH$^+$), Rt=4.47, purity: 89%.

1-[3-[[2-[5-(2-Propyl)- 1H-indol-3-yl]ethyl](2-propyl)amino]propyl]-1-(4-fluorophenyl)-1,3dihydroisobenzofuran-5-carbonitrile (13h): LC/MS (m/z) 524 (MH$^+$), Rt=4.78, purity: 96%.

1-[3-[[3-(4-Fluoro-7-methyl-1H-indol-3-yl)propyl](prop-2-en-1-yl)amino]propyl]-1-(4-fluorophenyl)-1,3-dihydroisobenzofuran-5-carbonitrile (13i): LC/MS (m/z) 526 (MH$^+$), Rt=4.65, purity: 83%.

1-[3-[[2-(4-Chloro-7-methyl-1H-indol-3-yl)ethyl](prop-2-en-1-yl)amino]propyl]-1-(4-fluorophenyl)-1,3-dihydroisobenzofuran-5-carbonitrile (13j): LC/MS (m/z) 528 (MH$^+$), Rt=4.67, purity: 79%.

1-[3-[[3-(5-Chloro-1H-indol-3-yl)propyl](prop-2-en-1-yl)amino]propyl]-1-(4-fluorophenyl)-1,3-dihydroisobenzofuran-5-carbonitrile (13k): LC/MS (m/z) 528 (MH$^+$), Rt=4.63, purity: 78%.

1-[3-[[2-(5-Pyrrolo[3,2-h]-1H-quinolin-3-yl)ethyl](prop-2-en-1-yl)amino]propyl]-1-(4-fluorophenyl)-1,3dihydroisobenzofuran-5-carbonitrile (13l): LC/MS (m/z) 531 (MH$^+$), Rt=3.43, purity: 91%.

1-[3-[[3-(7-Fluoro-1H-indol-3-yl)propyl](2-furylmethyl)amino]propyl]-1-(4-fluorophenyl)-1,3-dihydroisobenzofuran-5-carbonitrile (13m): LC/MS (m/z) 552 (MH$^+$), Rt=4.58, purity: 82%.

1-[3-[[4-(7-Carboxy-1H-indol-3-yl)butyl](prop-2-en-1-yl)amino]propyl]-1-(4-fluorophenyl)-1,3-dihydroisobenzofuran-5-carbonitrile (13n): LC/MS (m/z) 552 (MH$^+$), Rt=4.17, purity: 69%.

1-[3-[[2-[5-Bromo-1H-indol-3-yl]ethyl]-propylamino]propyl]-1-(4-fluorophenyl)-1,3-dihydroisobenzofuran-5-carbonitrile (13o): LC/MS (m/z) 560 (MH$^+$), Rt=4.62, purity: 96%.

1-[3-[[3-(1H-Indol-3-yl)propyl](2-phenoxyethyl)amino]propyl]-1-(4-fluorophenyl)-1,3-dihydroisobenzofuran-5-carbonitrile (13p): LC/MS (m/z) 574 (MH$^+$), Rt=4.78, purity: 93%.

1-[3-[[2-(5-Methyl-1H-indol-3-yl)ethyl](2-phenoxyethyl)amino]propyl]-1-(4-fluorophenyl)-1,3dihydroisobenzofuran-5-carbonitrile (13q): LC/MS (m/z) 574 (MH$^+$), Rt=4.82, purity: 93%.

1-[3-[[2-(5-Fluoro-1H-indol-3-yl)ethyl](2-phenoxyethyl)amino]propyl]-1-(4-fluorophenyl)-1,3-dihydroisobenzofuran-5-carbonitrile (13r): LC/MS (m/z) 578 (MH$^+$), Rt=4.71, purity: 95%.

1-[3-[[3-(1H-Pyrrolo[3,2-h]quinolin-3-yl)propyl](2-furylmethyl)amino]propyl]-1-(4-fluorophenyl)-1,3-dihydroisobenzofuran-5-carbonitrile (13s): LC/MS (m/z) 585 (MH$^+$), Rt=3.60, purity: 90%.

1-[3-[[3-(5-Methyl-1H-indol-3-yl)propyl](2-phenoxyethyl)amino]propyl]-1-(4-fluorophenyl)-1,3-dihydroisobenzofuran-5-carbonitrile (13t): LC/MS (m/z) 588 (MH$^+$), Rt=4.96, purity: 82%.

1-[3-[[3-(5-Fluoro-1H-indol-3-yl)propyl](2-phenoxyethyl)amino]propyl]-1-(4-fluorophenyl)-1,3-dihydroisobenzofuran-5-carbonitrile (13u): LC/MS (m/z) 592 (MH$^+$), Rt=4.82, purity: 90%.

1-[3-[[2-(5,7-Difluoro-1H-indol-3-yl)ethyl](2-phenoxyethyl)amino]propyl]-1-(4-fluorophenyl)-1,3-dihydroisobenzofuran-5-carbonitrile (13v): LC/MS (m/z) 596 (MH$^+$), Rt=4.84, purity: 92%.

1-[3-[[4-(1H-Pyrrolo[3,2-h]quinolin-3-yl)butyl](2-furylmethyl)amino]propyl]-1-(4-fluorophenyl)-1,3-dihydroisobenzofuran-5-carbonitrile (13w): LC/MS (m/z) 599 (MH$^+$), Rt=3.71, purity: 83%.

1-[3-[(2-Phenoxyethyl)[2-[5-(2-propyl)-1H-indol-3-yl]ethyl]amino]propyl]-1-(4-fluorophenyl)-1,3-dihydroisobenzofuran-5-carbonitrile (13x): LC/MS (m/z) 602 (MH$^+$), Rt=5.24, purity: 78%.

1-[3-[[2-(5-Bromo-1H-indol-3-yl)ethyl](2-phenoxyethyl)amino]propyl]-1-(4-fluorophenyl)-1,3-dihydroisobenzofuran-5-carbonitrile (13y): LC/MS (m/z) 638 (MH), Rt=4.98, purity: 91%.

Example 14

1-3-Iodopropyl)-1-(4-fluorophenyl)-1,3-dihydroisobenzofuran-5-carbonitrile (14a). A solution/suspension of 1-(3-chloropropyl)-1-(4-fluorophenyl)-1,3-dihydroisobenzofuran-5-carbonitrile (20 g, 35 mmol, 80% pure) and sodium iodide (285 g, 1.9 mol) in dry acetone (200 ml) was heated at reflux for 24 h. The mixture was evaporated, and partitioned between ether and water. The ether layer was separated, and was washed successively with water and brine. The organic extract was dried over anhydrous magnesium sulfate, filtered and evaporated to give 1-(3-iodopropyl)-1-(4-fluorophenyl)-1,3-dihydroisobenzofuran-5-carbonitrile (25.8 g, 99%, 80% pure) as a thick oil. $^1$H NMR (CDCl$_3$) δ 1.6–1.9 (m, 2H), 2.21 (ddd, 1H), 2.31 (ddd, 1H), 3.16 (td, 2H), 5.12 (dt, 1H), 5.21 (dt, 1H), 7.02 (t, 2H), 7.41 (d, 2H), 7.43 (d, 1H), 7.51 (s, 1H), 7.62 (dq, 1H)

The following compounds were prepared analogously:

1-(2-Iodoethyl)-1-(4-fluorophenyl)-1,3-dihydroisobenzofuran-5-carbonitrile (14b): yellow oil, $^1$H NMR (CDCl$_3$) δ 2.4–2.9 (m, 2H), 3.38 (dt, 1H), 3.46 (dt, 1H), 5.15 (d, 1H), 5.21 (d, 1H), 7.03 (t, 2H), 7.35–7.48 (m, 3H), 7.52 (s, 1H), 7.62 (d, 1H).

1-(4-Iodobutyl)-1-(4-fluorophenyl)-1,3-dihydroisobenzofuran-5-carbonitrile (14c): yellow oil, $^1$H NMR (CDCl$_3$) δ 1.1–1.5 (m, 2H), 1.81 (tt, 2H), 2.00–2.30 (m, 2H), 3.11 (t, 2H), 5.14 (d, 1H), 5.20 (d, 1H), 7.01 (t, 2H), 7.35–7.47 (m, 3H), 7.51 (s, 1H), 7.60 (d, 1H).

Example 15

1-(3-(Ethylamino)propyl)-1-(4-fluorophenyl)-1,3-dihydroisobenzofuran-5-carbonitrile (15a). To a stirred solution of 1-(3-iodopropyl)-1-(4-fluorophenyl)-1,3-dihydroisobenzofuran-5-carbonitrile (12.9 g, 30 mmol, 8% pure) in ethanol (150 mL) was added a solution of ethylamine (20.3 g, 450 mmol) in THF (50 mL) portionwise, and the mixture was stirred over night. The solution was evaporated, and was dissolved/suspended in water. The pH was adjusted to 12 using aqueous sodium hydroxide solution (2M) and was extracted with ether. The organic extract was washed with brine, dried over anhydrous magnesium sulfate, filtered and evaporated to give an oil. This oil was purified by silica chromatography using 50% v/v ethyl acetate/heptane as eluent, followed by 10% v/v triethylamine/40% v/v ethyl acetate/heptane followed by 20% v/v triethylamine/ethyl acetate to give the title compound (5.52 g, 57%) as a pale yellow oil. $^1$H NMR (CDCl$_3$) δ 1.05 (t, 3H), 1.2–1.6 (m, 2H), 2.15 (ddd, 1H), 2.24 (ddd, 1H), 2.57 (q, 2H) 2.58 (t, 2H), 5.12 (dt, 1H), 5.20 (dt, 1H), 7.00 (t, 2H), 7.38 (d, 1H), 7.42 (dd, 2H), 7.49 (s, 1H), 7.58 (ddt, 1H).

The following compounds were prepared analogously:

1-(2-(Methylamino)ethyl)-1-(4-fluorophenyl)-1,3-dihydroisobenzofuran-5-carbonitrile (15b): yellow oil; $^1$H NMR (CDCl$_3$) δ 2.38 (s, 3H), 2.33–2.72 (m, 4H), 5.13 (d, 1H), 5.20 (d, 1H), 7.01 (t, 2H), 7.37–7.47 (m, 3H), 7.50 (s, 1H), 7.59 (d, 1H).

1-(4-(Methylamino)butyl)-1-(4-fluorophenyl)-1,3-dihydroisobenzofuran-5-carbonitrile (15c): yellow oil; $^1$H NMR (CDCl$_3$) δ 1.00–1.45 (m, 2H), 1.46 (tt, 2H), 2.10 (ddd, 1H), 2.21 (ddd, 1H), 2.37 (s, 3H), 2.50 (t, 2H), 5.13 (d, 1H), 5.19 (d, 1H), 7.00 (t, 2H), 7.34–7.46 (m, 3H), 7.49 (s, 1H), 7.59 (d, 1H).

Pharmacological Testing

The affinity of the compounds of the invention to 5-HT$_{1A}$ receptors was determined by measuring the inhibition of binding of a radioactive ligand at 5-HT$_{1A}$ receptors as described in the following test:

Inhibition of $^3$H-5CT Binding to Human 5-HT$_{1A}$ Receptors

By this method the inhibition by drugs of the binding of the 5-HT$_{1A}$ agonist $^3$H-5-carboxamido tryptamine ($^3$H-5-CT) to cloned human 5-HT$_{1A}$ receptors stably expressed in transfected HeLa cells (HA7) (Fargin, A. et al, *J. Biol. Chem.*, 1989, 264, 14848) is determined in vitro. The assay was performed as a modification of the method described by Harrington, M. A. et al, *J. Pharmacol. Exp. Ther.*, 1994, 268, 1098. Human 5-HT$_{1A}$ receptors (40 μg of cell homogenate) were incubated for 15 minutes at 37° C. in 50 mM Tris buffer at pH 7.7 in the presence of $^3$H-5-CT. Non-specific binding was determined by including 10 μM of metergoline. The reaction was terminated by rapid filtration through Unifilter GF/B filters on a Tomtec Cell Harvester. Filters were counted in a Packard Top Counter. The results obtained are presented in table 1 below.

The compounds of the invention have also been tested for their effect on re-uptake of serotonin in the following test:
Inhibition of $^3$H-5HT Uptake Into Rat Brain Synaptosomes Using this method, the ability of drugs to inhibit the accumulation of $^3$H-5-HT into whole rat brain synaptosomes is determined in vitro. The assay was performed as described by Hyttel, J., *Psychopharmacology* 1978, 60, 13. The results obtained are presented in table 1:

TABLE 1

| Compound No. | Inhibition of $^3$H-5-CT binding IC$_{50}$ (nM) % inhibition at 100 nM | Inhibition of serotonin reuptake IC$_{50}$ (nM) % inhibition at 100 nM |
|---|---|---|
| 1a | 39 | 60 |
| 1b | 12 | 13 |
| 1c | 53 | 85 |
| 2a | 1.0 | 340 |
| 2b | 6.4 | 40 |
| 2e | 38 | 15 |
| 2f | 8.6 | 14 |
| 2g | 40 | 20 |
| 2j | 41 | 9.7 |
| 2m | 4.7 | Not tested |
| 2n | 15 | Not tested |
| 2o | 12 | 31 |
| 4a | 23 | 54 |
| 4b | 63 | 59% inh. at 100 nM |
| 4c | 11 | 4% inh. at 100 nM |
| 4d | 4.5 | 7% inh. at 100 nM |
| 4e | 17 | 160 |
| 4f | 1.6 | 4% inh. at 100 nM |
| 4g | 18 | 28% inh. at 100 nM |
| 4h | 3.2 | 69 |
| 4i | 1.9 | 26% inh. at 100 nM |
| 4j | 6.1 | 78 |
| 4k | 0.42 | 100 |
| 4l | 76% inh. at 100 nM | 27% inh. at 100 nM |
| 4m | 65% inh. at 100 nM | 74% inh. at 100 nM |
| 4n | 14 | 39% inh. at 100 nM |
| 4o | 26 | 73 |
| 4p | 19 | 6% inh. at 100 nM |
| 4q | 16 | 60% inh. at 100 nM |
| 4r | 11 | 19% inh. at 100 nM |
| 4s | 30 | 35 |
| 4t | 69% inh. at 100 nM | 73% inh. at 100 nM |
| 4u | 58% inh. at 100 nM | 44% inh. at 100 nM |
| 12b | 43 | 10 |
| 12c | 19 | 17 |
| 12d | 31 | 12 |
| 12f | 4.7 | 13 |
| 12i | 27 | 20 |
| 12j | 7.9 | 14 |
| 12k | 3.6 | 8.4 |
| 12o | 6.2 | 49% inh. at 100 nM |
| 12p | 19 | 11 |
| 12q | 12 | 6.3 |
| 12r | 16 | 47% inh. at 100 nM |
| 12s | 7.7 | 18 |

TABLE 1-continued

| Compound No. | Inhibition of $^3$H-5-CT binding IC$_{50}$ (nM) % inhibition at 100 nM | Inhibition of serotonin reuptake IC$_{50}$ (nM) % inhibition at 100 nM |
|---|---|---|
| 12u | 9.0 | 22 |
| 12v | 39 | 12 |
| 12x | 14 | 50% inh. at 100 nM |
| 12aa | 16 | 37% inh. at 100 nM |
| 12ab | 20 | 50% inh. at 100 nM |
| 12ad | 21 | 35% inh. at 100 nM |
| 12ae | 11 | 49% inh. at 100 nM |
| 12af | 31 | 38% inh. at 100 nM |
| 13b | 7.4 | 44 |
| 13c | 9.6 | 12 |
| 13d | 15 | 21 |
| 13e | 22 | 27 |
| 13f | 31 | 16% inh. at 100 nM |
| 13g | 18 | 49% inh. at 100 nM |
| 13j | 16 | 61% inh. at 100 nM |
| 13k | 19 | Not tested |
| 13p | 23 | Not tested |
| 13q | 12 | Not tested |
| 13r | 8.9 | Not tested |
| 13t | 23 | Not tested |
| 13u | 22 | Not tested |
| 13v | 23 | Not tested |
| 13x | 26 | Not tested |
| Pindolol* | 100 | |
| Paroxetine* | — | 0.29 |

Table 1 *reference compounds

Furthermore, the 5-HT$_{1A}$ antagonistic activity of some of the compounds of the invention has been estimated in vitro at cloned 5-HT$_{1A}$ receptors stably expressed in transfected HeLa cells (HA7). In this test, 5-HT$_{1A}$ antagonistic activity is estimated by measuring the ability of the compounds to antagonize the 5-HT induced inhibition of forskolin induced cAMP accumulation. The assay was performed as a modification of the method described by Pauwels, P. J. et al, *Biochem. Pharmacol.* 1993, 45, 375.

As seen from the above, the compounds of the invention show affinity for the 5-HT$_{1A}$ receptor. Furthermore, many of the compounds of the present invention possess valuable activity as serotonin re-uptake inhibitors.

Accordingly, the compounds are considered useful for the treatment of psychiatric and neurological disorders as mentioned previously.

Pharmaceutical Formulation

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 1000 mg. The total daily dose is usually in the range of about 0.05–500 mg, and most preferably about 0.1 to 50 mg of the active compound of the invention.

What is claimed is:

1. An isobenzofuran having the Formula I:

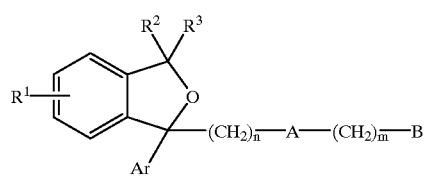

(I)

wherein

R$^1$ is hydrogen, halogen, trifluoromethyl, trifluoromethylsulfonyloxy, C$_{1-6}$ alkyl, C$_{2-6}$ alkenyl, C$_{2-6}$ alkynyl, C$_{3-8}$ cycloalkyl, C$_{1-6}$ alkoxy, hydroxy, formyl, —CO—C$_{1-6}$ alkyl, amino, C$_{1-6}$ alkylamino, C$_{2-12}$ dialkylamino, —NH—CO—C$_{1-6}$ alkyl, C$_{1-6}$ alkoxycarbonylamino, aminocarbonylamino, C$_{1-6}$ alkylaminocarbonylamino, C$_{2-12}$ dialkylaminocarbonylamino, nitro, cyano, COOH, or COO—C$_{1-6}$ alkyl;

R$^2$ and R$^3$ are each independently selected from hydrogen, trifluoromethyl, C$_{1-6}$ alkyl, C$_{2-6}$ alkenyl, C$_{2-6}$ alkynyl, C$_{3-8}$ cycloalkyl and C$_{1-6}$ alkoxy;

n is 1, 2, 3, 4 or 5;

m is 0 or 1;

A is selected from the following groups;

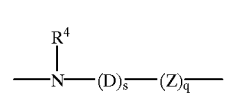

(1)

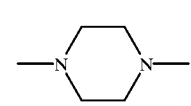

(2)

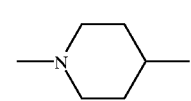

(3)

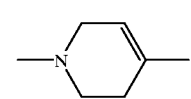

(4)

wherein

Z is O or S;

s is 0 or 1;

q is 0 or 1;

R$^4$ is hydrogen, C$_{1-6}$-alkyl, C$_{2-6}$-alkenyl, C$_{2-6}$-alkynyl, C$_{1-6}$-alkyl-phenyl, or C$_{1-6}$-alkyl-O-phenyl;

D is a spacer group selected from branched or straight chain $C_{1-6}$-alkylene, $C_{2-6}$-alkenylene and $C_{2-6}$-alkynylene;

B is a selected from the group of formula (II), (III) and (IV)

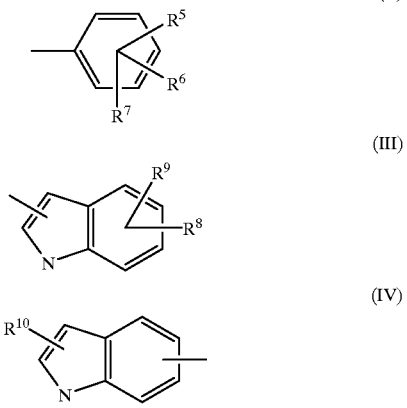

wherein $R^5$, $R^6$, $R^7$, $R^8$, $R^9$ and $R^{10}$ are each independently selected among the $R^1$ substituents;

or $R^8$ and $R^9$ together form a fused 5or 6-membered ring optionally containing further heteroatoms; and the resulting heterocycle is optionally substituted with substituents selected among the $R^1$ substituents;

or two of the groups of $R^5$, $R^6$ and $R^7$ are linked together thereby forming a —O—$(CH_2)$—O— bridge wherein p is 1 or 2;

Ar is independently selected from the group consisting of phenyl, 2-thienyl, 3-thienyl, 2-furanyl, 3-furanyl, 2-pyrimidyl, 1-indolyl, 2-indolyl, 3-indolyl, 1-indol-2-onyl, 3-indol-2-onyl, 2- or 3-benzofuranyl, 2- or 3-benzothiophenyl, 1-napthyl or 2-naphthyl, each optionally substituted with halogen, $C_{1-6}$ alkyl, $C_{1-6}$ alkoxy, $C_{1-6}$ alkylthio, hydroxy, $C_{1-6}$ alkylsulfonyl, cyano, trifluoromethyl, trifluoromethylsulfonyloxy, $C_{3-8}$ cycloalkyl, $C_{3-8}$ cycloalkyl-$C_{1-6}$ alkyl, nitro, amino, $C_{1-6}$ alkylamino, $C_{2-12}$ dialkylamino, acylamino or alkylenedioxy;

its enantiomers, and pharmaceutically acceptable acid addition salt thereof.

2. A compound of claim 1, wherein A is a group of formula (1).

3. A compound of claim 1, wherein A is a group of formula (2).

4. A compound of claim 1, wherein A is a group of formula (3).

5. A compound of claim 1, wherein A is a group of formula (4).

6. A compound of claim 2, wherein $R^4$ is selected from the group consisting of methyl, ethyl, propyl, 2-propen-1-yl, 2-furylmethyl, 2-phenoxyethyl.

7. A compound of claim 2, wherein q=0.

8. A compound of claim 2, wherein q=1 and Z is O.

9. A compound of claim 1, wherein B is a group of formula (II).

10. A compound of claim 1, wherein B is a group of formula (III).

11. A compound of claim 1, wherein B is a group of formula (IV).

12. A compound of claim 9, wherein at least one of $R^5$, $R^6$ and $R^7$, is methoxy.

13. A compound of claim 9, wherein Formula (II) is a benzodioxan group or a 1,2-methylenedioxybenzene group.

14. A compound of claim 10, wherein Formula (III) is a 3-indolyl.

15. A compound of claim 14, wherein the 3-indolyl is substituted in 5-position by methyl, fluoro, chloro, bromo, iodo, t-butyl or i-propyl, or in 7-position by fluoro, chloro or carboxy; or disubstituted by 5,7-difluoro, 4-fluoro-7-methyl or 4-chloro-7-methyl or the two substituents together form a pyridyl ring fused to the 3-indolyl.

16. A compound of claim 11, wherein Formula (IV) is a 4-indolyl or a 5-indolyl group.

17. A compound of claim 1, wherein Ar is phenyl or phenyl substituted with halogen or $CF_3$.

18. A compound of claim 17, wherein Ar is phenyl which may be substituted with Cl or F in the 4-position or Cl or $CF_3$ in the 3-position.

19. A compound of claim 1, wherein $R^1$ is H, CN or F in the 5-position of the isobenzofuran group.

20. A compound of claim 1, wherein $R^2$ and $R^3$ are selected from hydrogen or methyl.

21. A compound of claim 1, wherein n=2, 3 or 4.

22. A compound of claim 21, wherein n=3.

23. A compound of claim 1, wherein m=0.

24. A compound of claim 1, wherein $R^2$ and $R^3$ are both hydrogen; $R^1$ is H, CN or F in the 5-position of the isobenzofuran group; and Ar is phenyl which may be substituted with F or Cl in the 4-position or with Cl or $CF_3$ in the 3-position.

25. A compound of claim 1, wherein A is a group of formula (1); q=0; $R^4$ is methyl; D is propylene; m=0; and B is a 1,4-benzodioxan group of Formula (II) attached in the 5-position.

26. A compound of claim 1, wherein A is a group of formula (1); $R^4$ is $CH_3$ or prop-2-en-1-yl; n=3; D is ethylene or propylene; and B is a phenyl group wherein at least one substituent is OMe.

27. A compound of claim 1, wherein A is a group of formula (1); q is 0; $R^4$ is methyl, ethyl, propyl, 2-propen-1-yl, 2-furylmethyl or 2-phenoxyethyl; D is ethylene or propylene; m=0; and B is a 3-indolyl group of Formula (III).

28. A compound of claim 27, wherein the 3-indolyl group is substituted by methyl, fluoro, chloro, bromo, iodo, t-butyl or i-propyl in the 5-position; or fluoro, chloro or carboxy in the 7-position; or by 5,7-difluoro, 4-fluoro-7-methyl or 4-chloro-7-methyl; or the two substituents together form a pyridyl ring fused to the 3-indolyl-group.

29. A compound of claim 1, wherein A is a group of formula (2) or (3); n=3; m=0; and B is an 4- or 5-indolyl-group of Formula (IV) wherein $R^{10}$ is hydrogen; $R^1$ is CN in the 5-position of the isobenzofuran and Ar is 4-Fluorophenyl.

30. A compound of claim 1 which is selected from the group consisting of (−)-1-[3-[[4-(1,4-Benzodioxan-5-yl)butyl]methylamino]propyl]-1-(4-fluorophenyl)-1,3-dihydroisobenzofuran-5-carbonitrile, 1-[3-[[3-(1,4-Benzodioxan-5-yl)propyl]methylamino]propyl]-1-(4-fluorophenyl)-1,3-dihydroisobenzofuran-5-carbonitrile oxalate, 1-[3-[[2-(1,4-Benzodioxan-5-yl)ethyl]methylamino]propyl]-1-(4-fluorophenyl)-1,3-dihydroisobenzofuran-5-carbonitrile oxalate, 1-[3-[[1,4-Benzodioxan-5-ylmethyl]methylamino]propyl]-1-(4-fluorophenyl)-1,3-dihydroisobenzofuran-5-carbonitrile oxalate, 1-(4-Fluorophenyl)-1-[3-[4-(2-methoxyphenyl)piperazinyl]propyl]-1,3-dihydroisobenzofuran-5-carbonitrile, 1-(4-Fluorophenyl)-1-[3-[methyl[2-(2-methoxyphenoxy) ethyl]amino]propyl]-1,3-dihydroisobenzofuran-5-carbonitrile, 1-(4-Fluorophenyl)-1-[3-[methyl[2-(3-methoxyphenoxy) ethyl]amino]propyl]-1,3-dihydroisobenzofuran-5-carbonitrile, (S)-1-[3-[[4-(1H-Indol-3-yl)butyl]methylamino]propyl]-1-(4-fluorophenyl)-1,3-dihydroisobenzofuran-5-carbonitrile, 1-[3-[[4-(1H-Indol-3-yl)butyl]methylamino]propyl]-1-phenyl-1,3-dihydroisobenzofuran, (S)-1-[3-[[3-(1H-Indol-3-yl)propyl]methylamino] propyl]-1-(4-fluorophenyl)-1,3-dihydroisobenzofuran-5-carbonitrile, 1-[3-[[3-(1H-Indol-3-yl)propyl]methylamino]propyl]-1-phenyl-1,3-dihydroisobenzofuran, 5-[3-[[3-(1-Phenyl-1,3-dihydroisobenzofuran-1-yl) propyl]methylamino]propyl]-1,4-benzodioxane, 5-[3-[[3-[1-(3-Chlorophenyl)-1,3-dihydroisobenzofuran-1-yl]propyl]methylamino]propyl]-1,4-benzodioxane, 5-[3-[[3-[1-(4-Fluorophenyl)-1,3-dihydroisobenzofuran-1-yl]propyl]methylamino]propyl]-1,4-benzodioxane, 5-[3-[[3-[1-(3-Trifluoromethylphenyl)-1,3-dihydroisobenzofuran-1-yl]propyl]methylamino] propyl]-1,4-benzodioxane, 1-[3-[[3-(1,4-Benzodioxan-5-yl)propyl]methylamino] propyl]-1-(4-chlorophenyl)-1,3-dihydroisobenzofuran-5-carbonitrile, 1-[3-[4-(1H-Indol-4-yl)piperazinyl]propyl]-1-(4-fluorophenyl)-1,3-dihydroisobenzofuran-5-carbonitrile, 1-[3-[4-(1H-Indol-5-yl)piperazinyl]propyl]-1-(4-fluorophenyl)-1,3-dihydroisobenzofuran-5-carbonitrile, 1-[3-[4-(1H-Indol-3-yl)piperidinyl]propyl]-1-(4-fluorophenyl)-1,3-dihydroisobenzofuran-5-carbonitrile, 5-[3-[[3-[-5-Fluoro-1-(4-fluorophenyl)-1,3-dihydroisobenzofuran-1-yl]propyl]methylamino] propyl]-1,4-benzodioxane, 1-[3-[[2-(1H-Indolyl-3-yl)ethyl]methylamino]propyl]-1-(4-fluorophenyl)-1,3-dihydroisobenzofuran-5-carbonitrile, 1-(4-Fluorophenyl)-1-[3-[[2-(3-methoxyphenyl)ethyl] methylamino]propyl]-1,3-dihydroisobenzofuran-5-carbonitrile, 1-(4-Fluorophenyl)-1-[3-[[2-(3-methoxyphenyl)ethyl] (prop-2-en-1-yl)amino]propyl]-1,3-dihydroisobenzofuran-5-carbonitrile, 1-(4-Fluorophenyl)-1-[3-[[2-(2-methoxyphenyl)ethyl] (prop-2-en-1-yl)amino]propyl]-1,3-dihydroisobenzofuran-5-carbonitrile, 1-[3-[[2-(2,5-Dimethoxyphenyl)ethyl]methylamino] propyl]-1-(4-fluorophenyl)-1,3-dihydroisobenzofuran-5-carbonitrile, 1-[3-[[2-(2,5-Dimethoxyphenyl)ethyl](prop-2-en-1-yl) amino]propyl]-1-(4-fluorophenyl)-1,3-dihydroisobenzofuran-5-carbonitrile, 1-(4-Fluorophenyl)-1-[3-[[2-phenoxyethyl]methylamino] propyl]-1,3-dihydroisobenzofuran-5-carbonitrile, 1-[3-[[2-(1H-Indolyl-3-yl)ethyl](prop-2-en-1-yl)amino] propyl]-1-(4-fluorophenyl)-1,3-dihydroisobenzofuran-5-carbonitrile, 1-(4-Fluorophenyl)-1-[3-[[2-phenoxyethyl](prop-2-en-1-yl)amino]propyl]-1,3-dihydroisobenzofuran-5-carbonitrile, 1-(4-Fluorophenyl)-1-[3-[[3-(2-methoxyphenyl)propyl] methylamino]propyl]-1,3-dihydroisobenzofuran-5-carbonitrile, 1-(4-Fluorophenyl)-1-[3-[[3-(2-methoxyphenyl)propyl] (prop-2-en-1-yl)amino]propyl]-1,3-dihydroisobenzofuran-5-carbonitrile, 1-(4-Fluorophenyl)-1-[3-[[3-(3-methoxyphenyl)propyl] (prop-2-en-1-yl)amino]propyl]-1,3-dihydroisobenzofuran-5-carbonitrile, 1-(4-Fluorophenyl)-1-[3-[[3-(2-methoxyphenoxy)propyl] methylamino]propyl]-1,3-dihydroisobenzofuran-5-carbonitrile, 1-(4-Fluorophenyl)-1-[3-[[3-(2-methoxyphenoxy)propyl] (prop-2-en-1-yl)amino]propyl]-1,3-dihydroisobenzofuran-5-carbonitrile, 1-(4-Fluorophenyl)-1-[3-[[3-(3-methoxyphenoxy)propyl] methylamino]propyl]-1,3-dihydroisobenzofuran-5-carbonitrile, 1-(4-Fluorophenyl)-1-[3-[[3-(3-methoxyphenoxy)propyl] (prop-2-en-1-yl)amino]propyl]-1,3-dihydroisobenzofuran-5-carbonitrile, 1-[3-[(2-Benzyloxyethyl)methylamino]propyl]-1-(4-fluorophenyl)-1,3-dihydroisobenzofuran-5-carbonitrile, 1-[3-[(2-Benzyloxyethyl)(prop-2-en-1-yl)amino]propyl]-1-(4-fluorophenyl)-1,3-dihydroisobenzofuran-5-carbonitrile, 1-[3-[[3-(1H-Indolyl-3-yl)propyl](prop-2-en-1-yl)amino] propyl]-1-(4-fluorophenyl)-1,3-dihydroisobenzofuran-5-carbonitrile, 1-[3-[[3-(1H-Indolyl-3-yl)propyl](2-propynyl)amino] propyl]-1-(4-fluorophenyl)-1,3-dihydroisobenzofuran-5-carbonitrile, 1-[3-[[3-(1H-Indolyl-3-yl)propyl]methylamino]propyl]-1-(4-fluorophenyl)-1,3-dihydroisobenzofuran-5-carbonitrile, 1-[3-[[2-(5-Methyl-1H-indol-3-yl)ethyl]methylamino] propyl]-1-(4-fluorophenyl)-1,3-dihydroisobenzofuran-5-carbonitrile, 1-[3-[[2-(7-Fluoro-1H-indol-3-yl)ethyl]methylamino] propyl]-1-(4-fluorophenyl)-1,3-dihydroisobenzofuran-5-carbonitrile, 5-Fluoro-1-[3-[[3-(5-methyl-1H-indol-3-yl)propyl] methylamino]propyl]-1-(4-fluorophenyl)-1,3-dihydroisobenzofuran, 5-Fluoro-1-[3-[[3-(7-fluoro-1H-indol-3-yl)propyl] methylamino]propyl]-1-(4-fluorophenyl)-1,3-dihydroisobenzofuran, 1-[3-[[3-(5-Methyl-1H-indol-3-yl)propyl]methylamino] propyl]-1-(4-fluorophenyl)-1,3-dihydroisobenzofuran-5-carbonitrile, 1-3-[Ethyl[3-(1H-indol-3-yl)propyl]amino]propyl]-1-(4-fluorophenyl)-1,3-dihydroisobenzofuran-5-carbonitrile, 1-[3-[Ethyl[2-(5-methyl-1H-indol-3-yl)ethyl]amino] propyl]-1-(4-fluorophenyl)-1,3-dihydroisobenzofuran-5-carbonitrile, 1-[3-[[3-(7-Fluoro-1H-indol-3-yl)propyl]methylamino] propyl]-1-(4-fluorophenyl)-1,3-dihydroisobenzofuran-5-carbonitrile, 1-[3-[[3-(5-Fluoro-1H-indol-3-yl)propyl]methylamino]propyl]-1-(4-fluorophenyl)-1,3-dihydroisobenzofuran-5-carbonitrile, 1-[3-[Ethyl[2-(5-fluoro-1H-indol-3-yl)ethyl]amino]propyl]-1-(4-fluorophenyl)-1,3-dihydroisobenzofuran-5-carbonitrile, 1-[3-[Ethyl[2-(7-fluoro-1H-indol-3-yl)ethyl]amino]propyl]-1-(4-fluorophenyl)-1,3-dihydroisobenzofuran-5-carbonitrile, 1-[3-[[2-(5-Chloro-1H-indol-3-yl)ethyl]methylamino]propyl]-1-(4-fluorophenyl)-1,3-dihydroisobenzofuran-5-carbonitrile, 1-[3-[[3-(5-Chloro-1H-indol-3-yl)propyl]methylamino]propyl]-5-fluoro-1-(4-fluorophenyl)-1,3-dihydroisobenzofuran, 1-[3-[[4-(5-Methyl-1H-indol-3-yl)butyl]methylamino]propyl]-1-(4-fluorophenyl)-1,3-dihydroisobenzofuran-5-carbonitrile, 1-[3-[Ethyl[3-(5-methyl-1H-indol-3-yl)propyl]amino]propyl]-1-(4-fluorophenyl)-1,3-dihydroisobenzofuran-5-carbonitrile, 1-[3-[Ethyl[3-(7-fluoro-1H-indol-3-yl)propyl]amino]propyl]-1-(4-fluorophenyl)-1,3-dihydroisobenzofuran-5-carbonitrile, 1-[3-[Ethyl[3-(5-fluoro-1H-indol-3-yl)propyl]amino]propyl]-1-(4-fluorophenyl)-1,3-dihydroisobenzofuran-5-carbonitrile, 1-[3-[[3-(5-Chloro-1H-indol-3-yl)propyl]methylamino]propyl]-1-(4-fluorophenyl)-1,3-dihydroisobenzofuran-5-carbonitrile, 1-[3-[[2-(7-Chloro-1H-indol-3-yl)ethyl]ethylamino]propyl]-1-(4-fluorophenyl)-1,3-dihydroisobenzofuran-5-carbonitrile, 1-[3-[[2-(5-Chloro-1H-indol-3-yl)ethyl]ethylamino]propyl]-1-(4-fluorophenyl)-1,3-dihydroisobenzofuran-5-carbonitrile, 1-[3-[[2-(5,7-Difluoro-1H-indol-3-yl)ethyl]ethylamino]propyl]-1-(4-fluorophenyl)-1,3-dihydroisobenzofuran-5-carbonitrile, 1-[3-[[4-(5-Fluoro-1H-indol-3-yl)butyl]ethylamino]propyl]-1-(4-fluorophenyl)-1,3-dihydroisobenzofuran-5-carbonitrile, 1-[3-[[4-(5-Chloro-1H-indol-3-yl)butyl]methylamino]propyl]-1-(4-fluorophenyl)-1,3-dihydroisobenzofuran-5-carbonitrile, 1-[3-[[3-(5-Chloro-1H-indol-3-yl)propyl]ethylamino]propyl]-1-(4-fluorophenyl)-1,3-dihydroisobenzofuran-5-carbonitrile, 1-[3-[[3-(5,7-Difluoro-1H-indol-3-yl)propyl]ethylamino]propyl]-1-(4-fluorophenyl)-1,3-dihydroisobenzofuran-5-carbonitrile, 1-[3-[[2-(5-Bromo-1H-indol-3-yl)ethyl]methylamino]propyl]-1-(4-fluorophenyl)-1,3-dihydroisobenzofuran-5-carbonitrile, 1-[3-[[3-(5-Bromo-1H-indol-3-yl)propyl]methylamino]propyl]-1-(4-fluorophenyl)-1,3-dihydroisobenzofuran-5-carbonitrile, 1-[3-[[2-(5-Bromo-1H-indol-3-yl)ethyl]ethylamino]propyl]-1-(4-fluorophenyl)-1,3-dihydroisobenzofuran-5-carbonitrile, 1-[3-[[4-(5-Bromo-1H-indol-3-yl)butyl]methylamino]propyl]-1-(4-fluorophenyl)-1,3-dihydroisobenzofuran-5-carbonitrile, 1-[3-[[3-(5-Bromo-1H-indol-3-yl)propyl]methylamino]propyl]-1-(4-fluorophenyl)-1,3-dihydroisobenzofuran-5-carbonitrile, 1-[3-[Ethyl[2-(5-iodo-1H-indol-3-yl)ethyl]amino]propyl]-1-(4-fluorophenyl)-1,3-dihydroisobenzofuran-5-carbonitrile, 1-[3-[Ethyl[3-(5-iodo-1H-indol-3-yl)propyl]amino]propyl]-1-(4-fluorophenyl)-1,3-dihydroisobenzofuran-5-carbonitrile, 1-[2-[[4-(5-Chloro-1H-indol-3-yl)butyl]methylamino]ethyl]-1-(4-fluorophenyl)-1,3-dihydroisobenzofuran-5-carbonitrile, 1-[2-[[4-(5-Bromo-1H-indol-3-yl)butyl]methylamino]ethyl]-1-(4-fluorophenyl)-1,3-dihydroisobenzofuran-5-carbonitrile, 1-[4-[[2-(5,7-Difluoro-1H-indol-3-yl)ethyl]methylamino]butyl]-1-(4-fluorophenyl)-1,3-dihydroisobenzofuran-5-carbonitrile, 1-[4-[[2-(7-Chloro-1H-indol-3-yl)ethyl]methylamino]butyl]-1-(4-fluorophenyl)-1,3-dihydroisobenzofuran-5-carbonitrile, 1-[4-[[2-(5-Chloro-1H-indol-3-yl)ethyl]methylamino]butyl]-1-(4-fluorophenyl)-1,3-dihydroisobenzofuran-5-carbonitrile, 1-[4-[[2-(5-Bromo-1H-indol-3-yl)ethyl]methylamino]butyl]-1-(4-fluorophenyl)-1,3-dihydroisobenzofuran-5-carbonitrile, 1-[4-[[2-(5-Methyl-1H-indol-3-yl)ethyl]methylamino]butyl]-1-(4-fluorophenyl)-1,3-dihydroisobenzofuran-5-carbonitrile, 1-[4-[[2-(5-Iodo-1H-indol-3-yl)ethyl]methylamino]butyl]-1-(4-fluorophenyl)-1,3-dihydroisobenzofuran-5-carbonitrile, 1-[4-[[2-(5-t-Butyl-1H-indol-3-yl)ethyl]methylamino]butyl]-1-(4-fluorophenyl)-1,3-dihydroisobenzofuran-5-carbonitrile, 1-[4-[[2-(5-i-Propyl-1H-indol-3-yl)ethyl]methylamino]butyl]-1-(4-fluorophenyl)-1,3-dihydroisobenzofuran-5-carbonitrile, 1-[3-[[2-(5-Methyl-1H-indol-3-yl)ethyl](prop-2-en-1-yl)amino]propyl]-1-(4-fluorophenyl)-1,3-dihydroisobenzofuran-5-carbonitrile, 1-[3-[[2-(5-Fluoro-1H-indol-3-yl)ethyl](prop-2-en-1-yl)amino]propyl]-1-(4-fluorophenyl)-1,3-dihydroisobenzofuran-5-carbonitrile, 1-[3-[[2-(7-Fluoro-1H-indol-3-yl)ethyl] (prop-2-en-1-yl)amino]propyl]-1-(4-fluorophenyl)-1,3-dihydroisobenzofuran-5-carbonitrile, 1-[3-[[3-(5-Fluoro-1H-indol-3-yl)propyl] (prop-2-en-1-yl)amino]propyl]-1-(4-fluorophenyl)-1,3-dihydroisobenzofuran-5-carbonitrile, 1-[3-[[3-(7-Fluoro-1H-indol-3-yl)propyl](prop-2-en-1-yl)amino]propyl]-1-(4-fluorophenyl)-1,3-dihydroisobenzofuran-5-carbonitrile, 1-[3-[[2-(5-Chloro-1H-indol-3-yl)ethyl](prop-2-en-1-yl)amino]propyl]-1-(4-fluorophenyl)-1,3-dihydroisobenzofuran-5-carbonitrile, 1-[3-[[2-(5,7-Difluoro-1H-indol-3-yl)ethyl]-propylamino]propyl]-1-(4-fluorophenyl)-1,3-dihydroisobenzofuran-5-carbonitrile, 1-[3-[[2-[5-(2-Propyl)-1H-indol-3-yl]ethyl]-2-propylamino]propyl]-1-(4-fluorophenyl)-1,3-dihydroisobenzofuran-5-carbonitrile, 1-[3-[[3-(4-Fluoro-7-methyl-1H-indol-3-yl)propyl](prop-2-en-1-yl)amino]propyl]-1-(4-fluorophenyl)-1,3-dihydroisobenzofuran-5-carbonitrile, 1-[3-[[2-(4-Chloro-7-methyl-1H-indol-3-yl)ethyl](prop-2-en-1-yl)amino]propyl]-1-(4-fluorophenyl)-1,3-dihydroisobenzofuran-5-carbonitrile, 1-[3-[[3-(5-Chloro-1H-indol-3-yl)propyl](prop-2-en-1-yl)amino]propyl]-1-(4-fluorophenyl)-1,3-dihydroisobenzofuran-5-carbonitrile, 1-[3-[[2-(5-Pyrrolo[3,2-h]-1H-quinolin-3-yl)ethyl](prop-2-en-1-yl)amino]propyl]-1-(4-fluorophenyl)-1,3-dihydroisobenzofuran-5-carbonitrile, 1-[3-[[3-(7-Fluoro-1H-indol-3-yl)propyl](2-furylmethyl)amino]propyl]-1-(4-fluorophenyl)-1,3-dihydroisobenzofuran-5-carbonitrile, 1-[3-[[4-(7-Carboxy-1H-indol-3-yl)butyl](prop-2-en-1-yl)amino]propyl]-1-(4-fluorophenyl)-1,3-dihydroisobenzofuran-5-carbonitrile, 1-[3-[[2-[5-Bromo-1H-indol-3-yl]ethyl]-propylamino propyl]-1-(4-fluorophenyl)-1,3-dihydroisobenzofuran-5-carbonitrile, 1-[3-[[3-(1H-Indol-3-yl)propyl](2-phenoxyethyl)amino]propyl]-1-(4-fluorophenyl)-1,3-dihydroisobenzofuran-5-carbonitrile, 1-[3-[[2-(5-Methyl-1H-indol-3-yl)ethyl](2-phenoxyethyl)amino]propyl]-1-(4-fluorophenyl)-1,3-dihydroisobenzofuran-5-carbonitrile, 1-[3-[[2-(5-Fluoro-1H-indol-3-yl)ethyl](2-phenoxyethyl)amino]propyl]-1-(4-fluorophenyl)-1,3-dihydroisobenzofuran-5-carbonitrile, 1-[3-[[3-(5-Pyrrolo[3,2-h]-1H-quinolin-3-yl)propyl]-2-furylmethylamino]propyl]-1-(4-fluorophenyl)-1,3-dihydroisobenzofuran-5-carbonitrile, 1-[3-[[3-(5-Methyl-1H-indol-3-yl)propyl](2-phenoxyethyl)amino]propyl]-1-(4-fluorophenyl)-1,3-dihydroisobenzofuran-5-carbonitrile, 1-[3-[[3-(5-Fluoro-1H-indol-3-yl)propyl](2-phenoxyethyl)amino]propyl]-1-(4-fluorophenyl)-1,3-dihydroisobenzofuran-5-carbonitrile, 1-[3-[[2-(5,7-Difluoro-1H-indol-3-yl)ethyl](2-phenoxyethyl)amino]propyl]-1-(4-fluorophenyl)-1,3-dihydroisobenzofuran-5-carbonitrile, 1-[3-[[4-(5-Pyrrolo[3,2-h]-1H-quinolin-3-yl)butyl]-2-furylmethylamino]propyl]-1-(4-fluorophenyl)-1,3-dihydroisobenzofuran-5-carbonitrile, 1-[3-[2-Phenoxyethyl [2-[5-(2-propyl)-1H-indol-3-yl]ethyl]amino]propyl]-1-(4-fluorophenyl)-1,3-dihydroisobenzofuran-5-carbonitrile or 1-[3-[[2-(5-Bromo-1H-indol-3-yl)ethyl](2-phenoxyethyl)amino]propyl]-1-(4-fluorophenyl)-1,3-dihydroisobenzofuran-5-carbonitrile or an acid addition salt thereof.

31. A pharmaceutical composition comprising a compound of claim 1 or a pharmaceutically acceptable acid addition salt thereof and at least one pharmaceutically acceptable carrier or diluent.

32. A method for the treatment of a disorder or disease of a living animal body, wherein said disease or disorder is responsive to the effect of 5-HT$_{1A}$ receptors, said method comprising administering to said living animal body a therapeutically effective amount of a compound according to claim 1 or a pharmaceutically acceptable acid addition salt thereof.

33. The method of claim 32, wherein the disorder or disease is selected from the group consisting of depression, psychosis, anxiety disorders, panic disorder, obsessive compulsive disorder, impulse control disorder, aggression, ischaemia, senile dementia or social phobia.

34. The method of claim 32, wherein the living animal body is a human.

\* \* \* \* \*